(12) United States Patent
Hayashi et al.

(10) Patent No.: US 6,335,447 B1
(45) Date of Patent: Jan. 1, 2002

(54) QUINOLONECARBOXYLIC ACID DERIVATIVES OR SALTS THEREOF

(75) Inventors: Kazuya Hayashi; Tokunori Kito; Junichi Mitsuyama; Tetsumi Yamakawa, all of Toyama; Hiroshi Kuroda, Ishikawa; Hiroyo Kawafuchi, Toyama, all of (JP)

(73) Assignee: Toyama Chemical Co., Ltd., Tokyo (JP)

( * ) Notice: Subject to any disclaimer, the term of this patent is extended or adjusted under 35 U.S.C. 154(b) by 0 days.

(21) Appl. No.: 09/647,763
(22) PCT Filed: Apr. 6, 1999
(86) PCT No.: PCT/JP99/01799
   § 371 Date: Oct. 5, 2000
   § 102(e) Date: Oct. 5, 2000
(87) PCT Pub. No.: WO99/51588
   PCT Pub. Date: Oct. 14, 1999

(30) Foreign Application Priority Data

Apr. 6, 1998 (JP) ............................................. 10-110146
Nov. 30, 1998 (JP) ............................................ 10-340217

(51) Int. Cl.$^7$ ..................... C07D 453/02; C07D 215/16
(52) U.S. Cl. ...................... 546/134; 546/137; 546/153; 546/155
(58) Field of Search ................................ 546/134, 137, 546/153, 155

(56) References Cited

U.S. PATENT DOCUMENTS 4,959,363 A   9/1990   Wentland

FOREIGN PATENT DOCUMENTS

JP          3-145487       6/1991

OTHER PUBLICATIONS

Michael Reuman, et al. "Synthesis and Antibacterial Activity of Some Novel 1–Substituted 1,4–Dihydro–4–Oxo–7–Pyridinyl–3–Quinolinecarboxylic Acids. Potent Antistaphylococcal Agents" J. Med. Chem 1995, vol. 38, pp. 2531–2540.

Primary Examiner—Paul J. Killos
(74) Attorney, Agent, or Firm—Sughrue Mion, PLLC

(57) ABSTRACT

Novel quinolonecarboxylic acid derivatives of general formula (1) or salts thereof which have potent antibacterial effects on gram-positive bacteria in particular Propionibacterium acnes

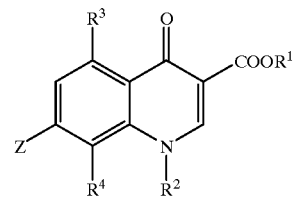

[1]

(wherein $R^1$ represents a hydrogen atom or a carboxyl-protective group; $R^2$ represents an optionally substituted cycloalkyl group; $R^3$ represents a hydrogen atom, a halogen atom, an optionally substituted alkyl, alkoxy or alkylthio group, an optionally protected hydroxyl or amino group, or a nitro group; $R^4$ represents an optionally substituted alkyl or alkoxy group; and Z represents a pyridin-4-yl or pyridin-3-yl group which is optionally substituted with at least one group selected from a halogen atom, an optionally substituted alkyl, alkenyl, cycloalkyl, alkoxy, alkylthio or amino group and an optionally protected hydroxyl or amino group).

7 Claims, No Drawings

QUINOLONECARBOXYLIC ACID DERIVATIVES OR SALTS THEREOF

TECHNICAL FIELD

The present invention relates to novel quinolonecarboxylic acid derivatives or salts thereof, particularly to quinolonecarboxylic acid derivatives or salts thereof exhibiting potent antibacterial activity against gram-positive bacteria, in particular Propionibacterium acnes.

BACKGROUND ART

4-Oxoquinoline-1,4-dihydro-3-carboxylic acid derivatives are known to have antibacterial activity. For example, 4-oxoquinoline-1,4-dihydro-3-carboxylic acid compounds having pyridine connected to the 7-position thereof through a carbon-to-carbon bond are described in Published Examined Japanese Patent Application (Kokoku) No. Sho-55-50591, Published Unexamined Japanese Patent Application No. Hei-1-100166, etc.

Furthermore, 4-oxoquinoline-1,4-dihydro-3-carboxylic compounds having a cyclopropyl group at the 1-position thereof include many known compounds including ciprofloxacin.

Moreover concerning 4-oxoqinoline-1,4-dihydro-3-carobxylic acid derivatives, i.e., so-called topical quinolone for skin, only nadifloxacin is used clinically.

Nadifloxacin and the compounds described in the above publications have insufficient activity against purulent disease-causing gram-positive bacteria such as staphylococci, in particular Propionibacterium acnes. Therefore, development of synthetic antibacterial agents having potent and broad antibacterial spectra against these bacteria is being desired.

On the other hand, the safety of quinolone antimicrobial agents, for example, phototoxicity and mutagenicity is being discussed [Journal of Antimicrobial Chemotherapy, 33, 685–706 (1994), Henigensei Shiken (Mutagenicity Tests), 2(3), 154–161 (1993)].

Accordingly, development of quinolone-based synthetic antibacterial agents having not only potent antibacterial activity and broad antibacterial spectrum but also increased safety is being desired.

DISCLOSURE OF THE INVENTION

Under the circumstances, the present inventors have made intensive research and as a result they have found that quinolonecarboxylic acid derivatives or salts thereof represented by general formula [1], which have a cycloalkyl group at the 1-position, a pyridine group connected through a carbon-to-carbon bond to the 7-position and an alkyl or alkoxy group at the 8-position of 4-oxoquinoline-3-carboxylic acid, have excellent antibacterial activity against various gram-positive bacteria such as staphylococci and gram-negative bacteria such as Escherichia coli, particularly excellent antibacterial activity against Propionibacterium acnes and have high safety. The present invention has been achieved based on this discovery.

That is, the present invention provides novel quinolonecarboxylic acid derivatives or salts thereof represented by the following general formula

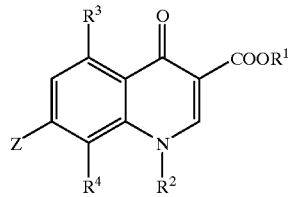

[1]

(wherein $R^1$ represents a hydrogen atom or a carboxyl-protective group; $R^2$ represents an optionally substituted cycloalkyl group; $R^3$ represents a hydrogen atom, a halogen atom, an optionally substituted alkyl, alkoxy or alkylthio group, an optionally protected hydroxyl or amino group, or a nitro group; $R^4$ represents an optionally substituted alkyl or alkoxy group; and Z represents a pyridin-4-yl or pyridin-3-yl group which may be substituted with at least one group selected from a halogen atom and an optionally substituted alkyl, alkenyl, cycloalkyl, alkoxy, alkylthio or amino group and an optionally protected hydroxyl or amino group).

Hereinafter, the compounds of the present invention will be described in detail.

Unless otherwise indicated specifically herein, the halogen atom means a fluorine atom, a chlorine atom, a bromine atom or an iodine atom; the alkyl group means a straight chain or branched chain $C_{1-6}$ alkyl group, such as methyl, ethyl, n-propyl, isopropyl, n-butyl, isobutyl, sec-butyl, tert-butyl or pentyl; the alkenyl group means a straight chain or branched chain $C_{2-6}$ alkenyl group, such as vinyl or allyl; the cycloalkyl group means a $C_{3-6}$ cycloalkyl group, such as cyclopropyl, cyclopentyl or cyclohexyl; the alkylene group means a $C_{1-6}$ alkylene group, such as methylene, ethylene or propylene; the alkoxy group means a straight chain or branched chain $C_{1-6}$ alkoxy group such as methoxy, ethoxy, n-propoxy, isopropoxy, n-butoxy, isobutoxy, sec-butoxy, tert-butoxy or pentyloxy; the alkylthio group means a straight chain or branched chain $C_{1-6}$ alkylthio group, such as methylthio, ethylthio, n-propylthio, isopropylthio, n-butylthio, isobutylthio, sec-butylthio, tert-butylthio or pentylthio; the alkylamino group means an amino group substituted with one or more straight chain or branched chain $C_{1-6}$ alkyl groups, such as methylamino, ethylamino, propylamino, butylamino, pentylamino, hexylamino, dimethylamino, diethylamino, methylethylamino, dipropylamino, dibutylamino or dipentylamino; the aryl group means phenyl, naphthyl or the like; the heterocyclic group means a 4-, 5-or 6-membered ring or condensed ring thereof including at least one hetero atom selected from an oxygen atom, a nitrogen atom and a sulfur atom as hetero atom or atoms which constitutes or constitute the ring, for example, oxetanyl, thietanyl, azetidinyl, furyl, pyrrolyl, thienyl, oxazolyl, isooxazolyl, imidazolyl, thiazolyl, isothiazolyl, pyrrolidinyl, benzofuranyl, benzothiazolyl, pyridyl, quinolyl, pyrimidinyl or morpholinyl group.

The cycloalkyl group in $R^2$; the alkyl group, alkoxy group or alkylthio group in $R^3$, the alkyl group or alkoxy group in $R^4$; the alkyl, alkenyl, cycloalkyl, alkoxy, alkylthio or amino group, which is a substituent group in pyridyl group in Z may be substituted with at least one group selected from a halogen atom, an optionally protected hydroxyl group, an optionally protected amino group, an optionally protected alkylamino group, an alkyl group, an alkoxy group, an aryl group, a cycloalkyl group and an alkenyl group and an alkyl group substituted with a halogen atom.

The carboxyl-protective group may include all the groups that can be usually used as a protective group for a carboxyl group, for example, alkyl groups such as methyl, ethyl, n-propyl, iso-propyl, 1,1-dimethylpropyl, n-butyl and tert-butyl; aryl groups such as phenyl and naphthyl; aralkyl groups such as benzyl, diphenylmethyl, trityl, p-nitrobenzyl, p-methoxybenzyl and bis(p-methoxyphenyl)methyl; acylalkyl groups such as acetylmethyl, benzoylmethyl, p-nitrobenzoylmethyl, p-bromobenzoylmethyl and p-methanesulfonylbenzoylmethyl; oxygen-containing heterocyclic groups such as 2-tetrahydropyranyl and 2-tetrahydrofuranyl; halogenoalkyl groups such as 2,2,2-trichloroethyl; alkylsilylalkyl groups such as 2-(trimethylsilyl)ethyl; acyloxyalkyl groups such as acetoxymethyl, propionyloxymethyl and pivaloyloxymethyl; nitrogen-containing heterocyclic alkyl groups such as phthalimidomethyl and succinimidomethyl; cycloalkyl groups such as cyclohexyl; alkoxyalkyl groups such as methoxymethyl, methoxyethoxymethyl and 2-(trimethylsilyl)ethoxymethyl; aralkoxyalkyl group such as benzyloxymethyl; alkylthioalkyl groups such as methylthiomethyl and 2-methylthioethyl; arylthioalkyl groups such as phenylthiomethyl; alkenyl groups such as 1,1-dimethyl-2-propenyl, 3-methyl-3-butenyl and allyl; and substituted silyl groups such as trimethylsilyl, triethylsilyl, triisopropylsilyl, diethylisopropylsilyl, tert-butyldimethylsilyl, tert-butyldiphenylsilyl, diphenylmethylsilyl and tert-butylmethoxyphenylsilyl, and the like.

The protective groups for the amino group and alkyl amino group may include all the groups that can be usually used as protective groups for amino groups, for example, acyl groups such as trichloroethoxycarbonyl, tribromoethoxycarbonyl, benzyloxycarbonyl, p-nitrobenzylcarbonyl, o-bromobenzyloxycarbonyl, (mono-, di-, tri)chloroacetyl, trifluoroacetyl, phenylacetyl, formyl, acetyl, benzoyl, tert-amyloxycarbonyl, tert-butoxycarbonyl, p-methoxybenzyloxycarbonyl, 3,4-dimethoxybenzyloxycarbonyl, 4-(phenylazo) benzyloxycarbonyl, 2-furfuryloxycarbonyl, diphenylmethoxycarbonyl, 1,1-dimethylpropoxycarbonyl, isopropoxycarbonyl, phthaloyl, succinyl, alanyl, leucyl, 1-adamantyloxycarbonyl and 8-quinolyloxycarbonyl; aralkyl groups such as benzyl, diphenylmethyl and trityl; arylthio groups such as 2-nitrophenylthio and 2,4-dinitrophenylthio; alkyl- or arylsulfonyl groups such as methanesulfonyl and p-toluenesulfonyl; dialkylaminoalkylidene groups such as N,N-dimethylaminomethylene; aralkylidene groups such as benzylidene, 2-hydroxybenzylidene, 2-hydroxy-5-chlorobenzylidene and 2-hydroxy-1-naphthylmethylene; nitrogen-containing heterocyclic aralkylidene groups such as 3-hydroxy-4-pyridylmethylene; cycloalkylidene groups such as cyclohexylidene, 2-ethoxycarbonylcyclohexylidene, 2-ethoxycarbonylcyclopentylidene, 2-acetylcyclohexylidene and 3,3-dimethyl-5-oxycyclohexylidene; diaryl-or diaralkylphosphoryl groups such as diphenylphosphoryl and dibenzylphosphoryl; oxygen-containing heterocyclic alkyl groups such as 5-methyl-2-oxo-2H-1,3-dioxol-4-ylmethyl; and substituted silyl groups such as trimethylsilyl, and the like.

The protective group for the hydroxyl group includes all the groups that can be usually used as a protective group for a hydroxyl group, for example, acyl groups such as benzyloxycarbonyl, 4-nitrobenzyloxycarbonyl, 4-bromobenzyloxycarbonyl, 4-methoxybenzyloxycarbonyl, 3,4-dimethoxybenzyloxycarbonyl, methoxycarbonyl, ethoxycarbonyl, tertbutoxycarbonyl, 1,1-dimethylpropoxycarbonyl, isopropoxycarbonyl, isobutyloxycarbonyl, diphenylmethoxycarbonyl, 2,2,2-trichloroethoxycarbonyl, 2,2,2-tribromoethoxycarbonyl, 2-(trimethylsilyl)ethoxycarbonyl, 2-(phenylsulfonyl) ethoxycarbonyl, 2-(triphenylphosphonio)ethoxycarbonyl, 2-furfuryloxycarbonyl, 1-adamantyloxycarbonyl, vinyloxycarbonyl, allyloxycarbonyl, S-benzylthiocarbonyl, 4-ethoxy-1-naphthyloxycarbonyl, 8-quinolyloxycarbonyl, acetyl, formyl, chloroacetyl, dichloroacetyl, trichloroacetyl, trifluoroacetyl, methoxyacetyl, phenoxyacetyl, pivaloyl and benzoyl; alkyl groups such as methyl, tert-butyl, 2,2,2-trichloroethyl and 2-trimethylsilylethyl; alkenyl groups such as allyl; aralkyl groups such as benzyl, p-methoxybenzyl, 3,4-dimethoxybenzyl, diphenylmethyl and trityl; oxygen-containing and sulfur-containing heterocyclic groups such as tetrahydrofuryl, tetrahydropyranyl and tetrahydrothiopyranyl; alkoxyalkyl groups such as methoxymethyl, benzyloxymethyl, 2-methoxyethoxymethyl, 2,2,2-trichloroethoxymethyl, 2-(trimethylsilyl) ethoxymethyl and 1-ethoxy-ethyl; alkyl-and arylsulfonyl groups such as methanesulfonyl and p-toluenesulfonyl; and substituted silyl groups such as trimethylsilyl, triethylsilyl, triisopropylsilyl, diethylisopropylsilyl, tert-butyldimethylsilyl, tert-butyldiphenylsilyl, diphenylmethylsilyl and tert-butylmethoxyphenylsilyl, and the like.

The salts of the compounds of general formula [1] include usually known salts of basic groups such as amino groups, or salts of acidic groups such as hydroxyl or carboxyl groups.

The salts of basic groups may include, for example, salts with mineral acids such as hydrochloric acid, hydrobromic acid and sulfuric acid; salts with organic carboxylic acids such as tartaric acid, formic acid, citric acid, trichloroacetic acid and trifluoroacetic acid; and acids with sulfonic acids such as methanesulfonic acid, benzenesulfonic acid, p-toluenesulfonic acid, mesitylenesulfonic acid and naphthalenesulfonic acid, and the like.

The salts of acidic groups may include, for example, salts with alkali metals such as sodium and potassium; salts with alkaline earth metals such as calcium and magnesium; ammonium salts; and salts with nitrogen-containing organic bases such as trimethylamine, triethylamine, tributylamine, pyridine, N,N-dimethylaniline, N-methylpiperidine, N-methylmorpholine, diethylamine, dicyclohexylamine, procain, dibenzylamine, N-benzyl-β-phenethylamine, 1-ephenamine and N,N'-dibenzylethylenediamine, and the like.

Among the above salts, preferred salts of the compounds of general formula [1] include pharmacologically acceptable salts.

Typical compounds of the present invention include, for example, the following compounds.

Abbreviations have the following meanings. Me: methyl, Et: ethyl, diMe: dimethyl, triMe: trimethyl, Cbz: benzyloxycarbonyl, cyclopropyl: cyclopropyl, pyridyl: pyridyl, oxide: oxide, $diNH_2$: diamino.

Groups in the brackets in Z stand for substituent groups for a pyridyl group.

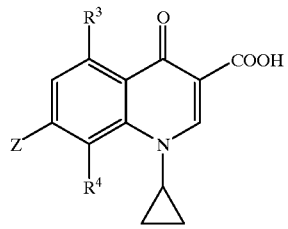

| No. | R³ | R⁴ | Z |
|---|---|---|---|
| 1. | H | Me | 3-Pyridyl |
| 2. | H | Me | (6-Me),3-Pyridyl |
| 3. | H | Me | (6-Et),3-Pyridyl |
| 4. | H | Me | (5-Me),3-Pyridyl |
| 5. | H | Me | (5-CH₂OH),3-Pyridyl |
| 6. | H | Me | (6-NH₂),3-Pyridyl |
| 7. | H | Me | (5-NH₂),3-Pyridyl |
| 8. | H | Me | (6-OMe),3-Pyridyl |
| 9. | H | Me | (6-NHMe),3-Pyridyl |
| 10. | H | Me | (6-NMe₂),3-Pyridyl |
| 11. | H | Me | (6-CH=CH₂),3-Pyridyl |
| 12. | H | Me | (6-Cl),3-Pyridyl |
| 13. | H | Me | (6-cyclopropyl),3-Pyridyl |
| 14. | H | Me | (6-SMe),3-Pyridyl |
| 15. | H | Me | (5,6-diMe),3-Pyridyl |
| 16. | H | Me | (4,6-diMe),3-Pyridyl |
| 17. | H | Me | (4,5,6-triMe),3-Pyridyl |
| 18. | H | Me | (6-Me,5-Et),3-Pyridyl |
| 19. | H | Me | (5-Me,6-NH₂),3-Pyridyl |
| 20. | H | Me | (5-Me,6-NHMe),3-Pyridyl |
| 21. | H | Me | (5-Me,6-NMeEt),3-Pyridyl |
| 22. | H | Me | (5-Me,6-NMe₂),3-Pyridyl |
| 23. | H | Me | (5,6-diNH₂),3-Pyridyl |
| 24. | H | Me | (5-Me,6-CH₂NMeCbz),3-Pyridyl |
| 25. | H | Me | (5-Me,6-CH₂NH₂),3-Pyridyl |
| 26. | H | Me | (5-Me,6-CH₂OH),3-Pyridyl |
| 27. | Me | Me | 3-Pyridyl |
| 28. | Me | Me | (6-Me),3-Pyridyl |
| 29. | Me | Me | (6-Et),3-Pyridyl |
| 30. | Me | Me | (5-Me),3-Pyridyl |
| 31. | Me | Me | (5-CH₂OH),3-Pyridyl |
| 32. | Me | Me | (6-NH₂),3-Pyridyl |
| 33. | Me | Me | (5-NH₂),3-Pyridyl |
| 34. | Me | Me | (6-OMe),3-Pyridyl |
| 35. | Me | Me | (6-NHMe),3-Pyridyl |
| 36. | Me | Me | (6-CH=CH₂),3-Pyridyl |
| 37. | Me | Me | (6-Cl),3-Pyridyl |
| 38. | Me | Me | (6-cyclopropyl),3-Pyridyl |
| 39. | Me | Me | (6-SMe),3-Pyridyl |
| 40. | Me | Me | (5,6-diMe),3-Pyridyl |
| 41. | Me | Me | (4,6-diMe),3-Pyridyl |
| 42. | Me | Me | (4,5,6-triMe),3-Pyridyl |
| 43. | Me | Me | (6-Me,5-Et),3-Pyridyl |
| 44. | Me | Me | (5-Me,6-NH₂),3-Pyridyl |
| 45. | Me | Me | (5-Me,6-NHMe),3-Pyridyl |
| 46. | Me | Me | (5-Me,6-NMeEt),3-Pyridyl |
| 47. | Me | Me | (5-Me,6-NMe₂),3-Pyridyl |
| 48. | Me | Me | (5,6-diNH₂),3-Pyridyl |
| 49. | Me | Me | (5-Me,6-CH₂NMeCbz),3-Pyridyl |
| 50. | Me | Me | (5-Me,6-CH₂NH₂),3-Pyridyl |
| 51. | Me | Me | (5-Me,6-CH₂OH),3-Pyridyl |
| 52. | NH₂ | Me | 3-Pyridyl |
| 53. | NH₂ | Me | (6-Me),3-Pyridyl |
| 54. | NH₂ | Me | (6-Et),3-Pyridyl |
| 55. | NH₂ | Me | (5-Me),3-Pyridyl |
| 56. | NH₂ | Me | (5-CH₂OH),3-Pyridyl |
| 57. | NH₂ | Me | (6-NH₂),3-Pyridyl |
| 58. | NH₂ | Me | (5-NH₂),3-Pyridyl |
| 59. | NH₂ | Me | (6-OMe),3-Pyridyl |
| 60. | NH₂ | Me | (6-NHMe),3-Pyridyl |
| 61. | NH₂ | Me | (6-CH=CH₂),3-Pyridyl |
| 62. | NH₂ | Me | (6-Cl),3-Pyridyl |
| 63. | NH₂ | Me | (6-cyclopropyl),3-Pyridyl |
| 64. | NH₂ | Me | (6-SMe),3-Pyridyl |

-continued

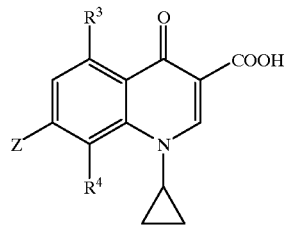

| No. | R³ | R⁴ | Z |
|---|---|---|---|
| 65. | NH₂ | Me | (5,6-diMe),3-Pyridyl |
| 66. | NH₂ | Me | (4,6-diMe),3-Pyridyl |
| 67. | NH₂ | Me | (4,5,6-triMe),3-Pyridyl |
| 68. | NH₂ | Me | (6-Me,5-Et),3-Pyridyl |
| 69. | NH₂ | Me | (5-Me,6-NH₂),3-Pyridyl |
| 70. | NH₂ | Me | (5-Me,6-NHMe),3-Pyridyl |
| 71. | NH₂ | Me | (5-Me,6-NMeEt),3-Pyridyl |
| 72. | NH₂ | Me | (5-Me,6-NMe₂),3-Pyridyl |
| 73. | NH₂ | Me | (5,6-diNH₂),3-Pyridyl |
| 74. | NH₂ | Me | (5-Me,6-CH₂NMeCbz),3-Pyridyl |
| 75. | NH₂ | Me | (5-Me,6-CH₂NH₂),3-Pyridyl |
| 76. | NH₂ | Me | (5-Me,6-CH₂OH),3-Pyridyl |
| 77. | H | OMe | (6-Me),3-Pyridyl |
| 78. | H | OMe | (5-Me),3-Pyridyl |
| 79. | H | OMe | (6-NH₂),3-Pyridyl |
| 80. | H | OMe | (5-NH₂),3-Pyridyl |
| 81. | H | OMe | (6-OMe),3-Pyridyl |
| 82. | H | OMe | (6-NHMe),3-Pyridyl |
| 83. | H | OMe | (5,6-diMe),3-Pyridyl |
| 84. | H | OMe | (6-Me,5-Et),3-Pyridyl |
| 85. | H | OMe | (5-Me,6-NH₂),3-Pyridyl |
| 86. | H | OMe | (5-Me,6-NHMe),3-Pyridyl |
| 87. | H | OMe | (5-Me,6-NMe₂),3-Pyridyl |
| 88. | H | OMe | (5,6-diNH₂),3-Pyridyl |
| 89. | H | OCHF₂ | (6-Me),3-Pyridyl |
| 90. | H | OCHF₂ | (5-Me),3-Pyridyl |
| 91. | H | OCHF₂ | (6-NH₂),3-Pyridyl |
| 92. | H | OCHF₂ | (5-NH₂),3-Pyridyl |
| 93. | H | OCHF₂ | (6-OMe),3-Pyridyl |
| 94. | H | OCHF₂ | (6-NHMe),3-Pyridyl |
| 95. | H | OCHF₂ | (5,6-diMe),3-Pyridyl |
| 96. | H | OCHF₂ | (6-Me,5-Et),3-Pyridyl |
| 97. | H | OCHF₂ | (5-Me,6-NH₂),3-Pyridyl |
| 98. | H | OCHF₂ | (5-Me,6-NHMe),3-Pyridyl |
| 99. | H | OCHF₂ | (5-Me,6-NMe₂),3-Pyridyl |
| 100. | H | OCHF₂ | (5,6-diNH₂),3-Pyridyl |
| 101. | H | Me | 4-Pyridyl |
| 102. | H | Me | (6-Me),4-Pyridyl |
| 103. | H | Me | (6-NH₂),4-Pyridyl |
| 104. | H | Me | (6-OMe),4-Pyridyl |
| 105. | H | Me | (6-NHMe),4-Pyridyl |
| 106. | H | Me | (6-CH=CH₂),4-Pyridyl |
| 107. | H | Me | (6-Cl),4-Pyridyl |
| 108. | H | Me | (6-cyclopropyl),4-Pyridyl |
| 109. | H | Me | (6-SMe),4-Pyridyl |
| 110. | H | Me | (2,6-diMe),4-Pyridyl |
| 111. | H | Me | (2-Et,6-Me),4-Pyridyl |
| 112. | H | Me | (2-CH₂OH,6-Me),4-Pyridyl |
| 113. | H | Me | (2-CH₂NH₂,6-Me),4-Pyridyl |
| 114. | H | Me | (2-CH₂NHMe,6-NMe₂),4-Pyridyl |
| 115. | H | Me | (2-CH₂NMe₂,6-Me),4-Pyridyl |
| 116. | Me | Me | 4-Pyridyl |
| 117. | Me | Me | (6-Me),4-Pyridyl |
| 118. | Me | Me | (6-NH₂),4-Pyridyl |
| 119. | Me | Me | (6-OMe),4-Pyridyl |
| 120. | Me | Me | (6-NHMe),4-Pyridyl |
| 121. | Me | Me | (6-CH=CH₂),4-Pyridyl |
| 122. | Me | Me | (6-Cl),4-Pyridyl |
| 123. | Me | Me | (6-cyclopropyl),4-Pyridyl |
| 124. | Me | Me | (6-SMe),4-Pyridyl |
| 125. | Me | Me | (2,6-diMe),4-Pyridyl |
| 126. | Me | Me | (2-Et,6-Me),4-Pyridyl |
| 127. | Me | Me | (2-CH₂OH,6-Me),4-Pyridyl |
| 128. | Me | Me | (2-CH₂NH₂,6-Me),4-Pyridyl |

-continued

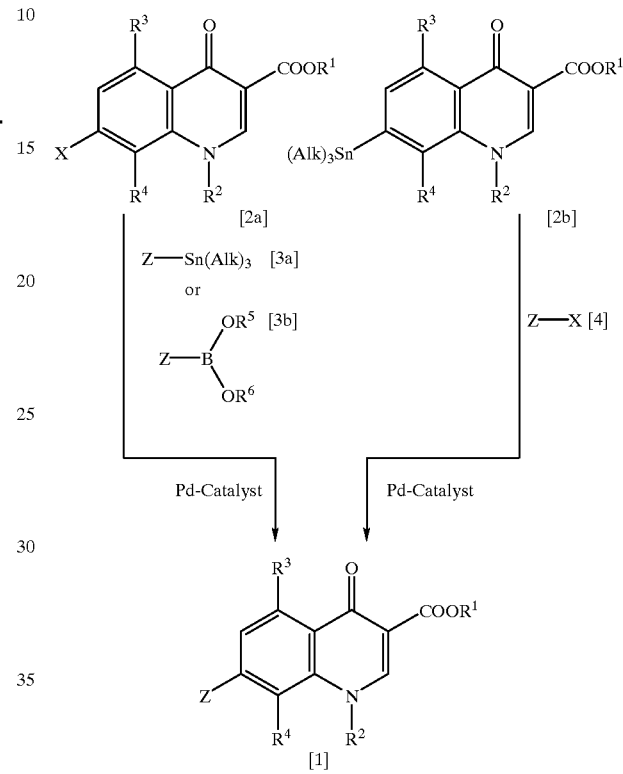

| No. | R³ | R⁴ | Z |
|---|---|---|---|
| 129. | Me | Me | (2-CH₂NHMe,6-NMe₂),4-Pyridyl |
| 130. | Me | Me | (2-CH₂NMe₂,6-Me),4-Pyridyl |
| 131. | NH₂ | Me | 4-Pyridyl |
| 132. | NH₂ | Me | (6-Me),4-Pyridyl |
| 133. | NH₂ | Me | (6-NH₂),4-Pyridyl |
| 134. | NH₂ | Me | (6-OMe),4-Pyridyl |
| 135. | NH₂ | Me | (6-NHMe),4-Pyridyl |
| 136. | NH₂ | Me | (6-CH=CH₂),4-Pyridyl |
| 137. | NH₂ | Me | (6-Cl),4-Pyridyl |
| 138. | NH₂ | Me | (6-cyclopropyl),4-Pyridyl |
| 139. | NH₂ | Me | (6-SMe),4-Pyridyl |
| 140. | NH₂ | Me | (2,6-diMe),4-Pyridyl |
| 141. | NH₂ | Me | (2-Et,6-Me),4-Pyridyl |
| 142. | NH₂ | Me | (2-CH₂OH,6-Me),4-Pyridyl |
| 143. | NH₂ | Me | (2-CH₂NH₂,6-Me),4-Pyridyl |
| 144. | NH₂ | Me | (2-CH₂NHMe,6-NMe₂),4-Pyridyl |
| 145. | NH₂ | Me | (2-CH₂NMe₂,6-Me),4-Pyridyl |
| 146. | H | OMe | (6-NH₂),4-Pyridyl |
| 147. | H | OMe | (6-OMe),4-Pyridyl |
| 148. | H | OMe | (2,6-diMe),4-Pyridyl |
| 149. | H | OCHF₂ | (6-NH₂),4-Pyridyl |
| 150. | H | OCHF₂ | (6-OMe),4-Pyridyl |
| 151. | H | OCHF₂ | (2,6-diMe),4-Pyridyl |
| 152. | H | Me | 3-Pyridyl-N-oxide |
| 153. | H | Me | 4-Pyridyl-N-oxide |
| 154. | H | Me | (5,6-diMe),3-Pyridyl-N-oxide |
| 155. | H | Me | (2,6-diMe),4-Pyridyl-N-oxide |
| 156. | Me | Me | 3-Pyridyl-N-oxide |
| 157. | Me | Me | 4-Pyridyl-N-oxide |
| 158. | Me | Me | (5,6-diMe),3-Pyridyl-N-oxide |
| 159. | Me | Me | (2,6-diMe),4-Pyridyl-N-oxide |
| 160. | NH₂ | Me | 3-Pyridyl-N-oxide |
| 161. | NH₂ | Me | 4-Pyridyl-N-oxide |
| 162. | NH₂ | Me | (5,6-diMe),3-Pyridyl-N-oxide |
| 163. | NH₂ | Me | (2,6-diMe),4-Pyridyl-N-oxide |

In the present invention, those compounds in which $R^2$ is an optionally substituted cyclopropyl group; $R^3$ is a hydrogen atom, an optionally substituted alkyl group or an optionally protected amino group; $R^4$ is an optionally substituted alkyl or alkoxy group; Z is a pyridin-4-yl or pyridin-3-yl group substituted with an optionally substituted alkyl, alkoxy or amino group are preferred.

Furthermore, those compounds in which $R^2$ is a cyclopropyl group; $R^3$ is a hydrogen atom, an alkyl group or an amino group; $R^4$ is an alkyl or alkoxy group; Z is a pyridin-3-yl group substituted with an optionally substituted alkyl, alkoxy or amino group are preferred.

Moreover, those compounds in which $R^2$ is a cyclpropyl group; $R^3$ is a hydrogen atom; $R^4$ is a methyl or methoxy group; Z is a pyridin-3-yl group substituted with at least one group selected from a methyl group, a hydroxymethyl group, an amino group, a methylamino group or a dimethylamino group are preferred.

Where the compounds of general formula [1] or salts thereof have isomers (for example, optical isomers, geometrical isomers and tautomers), the present invention includes such isomers and also include solvates, hydrates and various forms of crystals.

Next, production methods of the compounds of the present invention will be described.

The compounds of the present invention can be synthesized, for example, by the following production methods.

Production Method 1

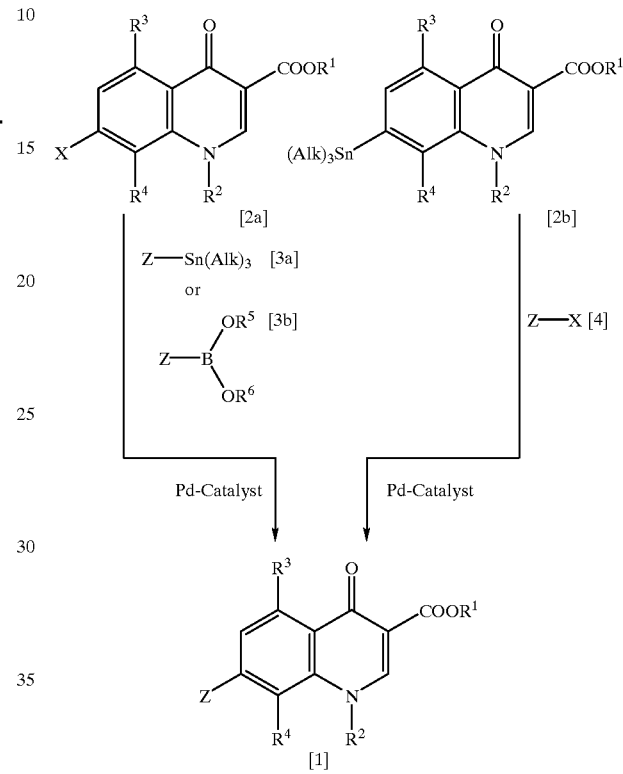

Production Method 2

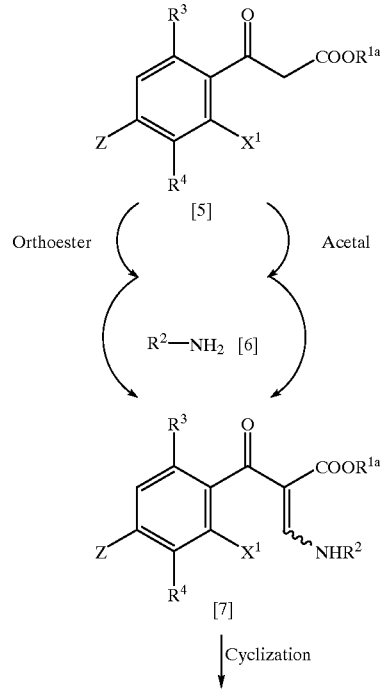

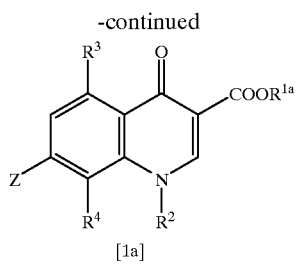

Production Method 3

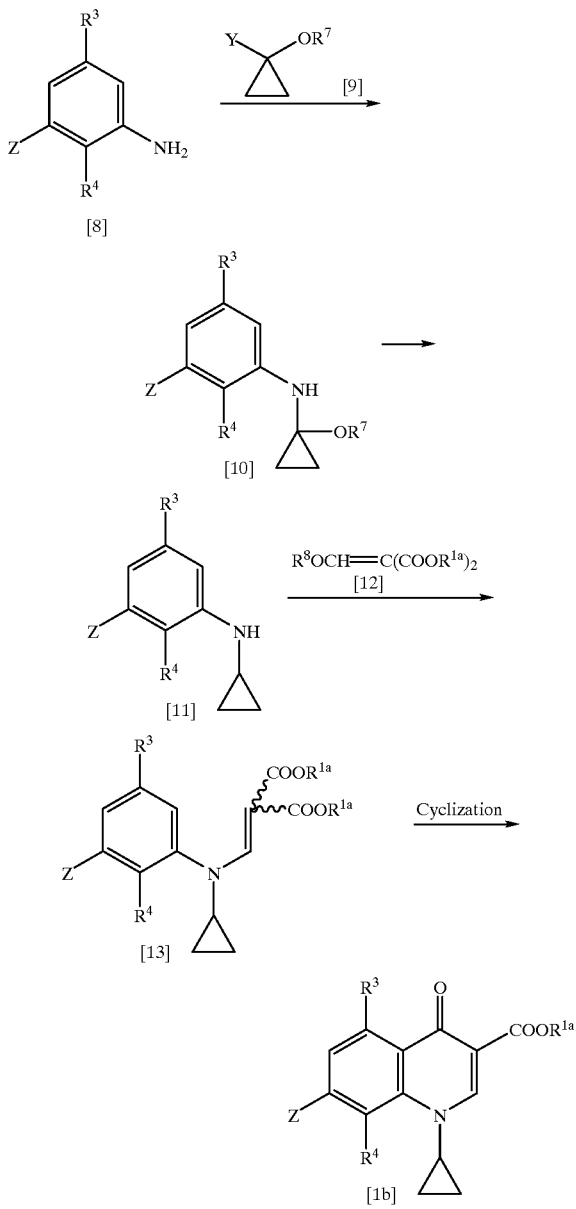

(In the above formulae, $R^1$, $R^2$, $R^3$, $R^4$ and Z have the same meanings as defined above; $R^5$ and $R^6$, which may be the same or different, represent a hydrogen atom, an alkyl group, or $R^5$ and $P^6$ together form a ring containing a boron atom; $R^7$ represents an alkyl group; $R^8$ represents an alkyl group; Y represents a halogen atom or a trialkylsilyloxy group; X represents a leaving group; Alk represents an alkyl group; $X^1$ represents a halogen atom; $R^{1a}$ represents the same carboxyl-protective group as $R^1$.)

The leaving group includes a chlorine atom, a bromine atom, an iodine atom, a methylsulfonyloxy group, a trifluoromethylsulfonyloxy group and a p-fluorophenylsulfonyloxy group, etc.

The trialkylsilyloxy group includes tri-$C_{1-5}$-alkylsilyloxy groups such as trimethylsilyloxy and triethylsilyloxy.

The ring containing a boron atom formed by $R^5$ and $R^6$ together includes 5- to 8-membered rings and condensed rings thereof, containing at least one hereto atom selected from an oxygen atom and a nitrogen atom as hetero atom or atoms constituting the ring, for example, 1,3,2-dioxaborolane, 1,3,2-dioxaborinane, 4H-dihydro-1,3,5,2-dioxaazaborinane, 1,3,5,2-trioxaborinane, 1,3,6,2-trioxaborocane and 1,3,6,2-dioxaazaborocane, etc.

The compounds of general formulae [1a] and [1b] may be in the form of salts. The salts may include the same salts as described on the compounds of general formula [1].

[Production Method 1] (1-a) The compounds of general formula [1] can be obtained by subjecting the compound of general formula [2a] and the compound of general formula [3a] to coupling reaction, or by subjecting the compound of general formula [2b] and the compound of general formula [4] to coupling reaction, in the presence or absence of silver oxide using a palladium catalyst.

The solvent used in the reaction is not particularly limited as far as it does not adversely affect the reaction. It includes, for example, aromatic hydrocarbons such as benzene, toluene and xylene; ethers such as dioxane, tetrahydrofuran, anisole, diethylene glycol diethyl ether and dimethyl cellosolve; nitriles such as acetonitrile, amides such as N,N-dimethylformamide, N,N-dimethylacetamide and 1-methyl-2-pyrrolidone; and sulfoxides such as dimethyl sulfoxide, and the like. These may be used in admixture.

The palladium catalyst used in the reaction includes, for example, metallic palladium such as palladium-activated carbon and palladium black; inorganic palladium salts such as palladium chloride; organic palladium salts such as palladium acetate; and organic palladium complexes such as tetrakis(triphenylphosphine)palladium (0), bis(triphenylphosphine)palladium (II) chloride, bis(tricyclohexylphosphine)palladium (II) chloride and 1,1'-bis(diphenylphosphino)ferrocene palladium (II) chloride, and the like.

The use amount of palladium catalyst may be 0.00001 fold by mole or more, preferably 0.001 to 0.05 fold by mole, based on the compound of general formula [2a] or [2b].

When silver oxide is used in the reaction, the use amount of it may be equimolar or more, preferably 1 to 10 fold by mole, based on the compound of general formula [2a] or [2b].

The use amount of the organic tin of general formula [3a] may be equimolar or more, preferably $1.0$ to 2.0 fold by mole, based on the compound of general formula [2a].

The use amount of the compound of general formula [4] may be equimolar or more, preferably 1.0 to 5.0 fold by mole, based on the compound of general formula [2b].

The coupling reaction may be practiced usually in an inert gas (for example, argon, nitrogen) atmosphere at 50 to 170° C. for 1 minute to 24 hours. (1-b) As an alternative method, the compounds of general formula [1] can be obtained by subjecting the compound of general formula [2a] and the compound of general formula [3b] to coupling reaction in the presence or absence of a base using a palladium catalyst or a nickel catalyst.

The solvent used in the reaction is not limited particularly as far as it does not adversely affect the reaction. It includes, for example, water; alcohols such as methanol, ethanol and propanol; aromatic hydrocarbons such as benzene, toluene and xylene; halogenated hydrocarbons such as methylene chloride, chloroform and dichloroethane; ethers such as 1,2-dimethoxyethane, dioxane, tetrahydrofuran, anisole, diethylene glycol diethyl ether and dimethyl cellosolve; esters such as ethyl acetate and butyl acetate; ketones such as acetone and methyl ethyl ketone; nitrites such as acetonitrile; amides such as N,N-dimethylformamide, N,N-dimethylacetamide and 1-methyl-2-pyrrolidone; and sulfoxides such as dimethyl sulfoxide, and the like. These may be used in admixture.

In the reaction, the optionally used base includes, for example, sodium hydrogen carbonate, sodium carbonate, potassiumcarbonate, tripotassiumphosphate, cesiumcarbonate, cesium fluoride, potassium fluoride, sodium fluoride and triethylamine. The use amount of the base may be equimolar or more, preferably 2 to 5 fold by mole, based on the compound of general formula [2a].

The palladium catalyst used in the reaction may be the same catalyst as described in (1-a) above.

The nickel catalyst used in the reaction includes, for example, organic nickel complexes such as bis(diphenylphosphino)ethane nickel (II) chloride, bis(diphenylphosphino)propane nickel (II) chloride, bis(diphenylphosphino)butane nickel (II) chloride, bis(triphenylphosphine) nickel (II) chloride and 1,1'-bis(diphenylphosphino)ferrocene nickel (II) chloride.

The use amount of the compound of general formula [3b] may be equimolar or more, preferably $1.0$ to $1.5$ folds by mole, base on the compound of general formula [2a].

The use amount of the palladium catalyst or nickel catalyst may be 0.00001 fold by mole or more, preferably 0.001 to 0.05 fold by mole, based on the compound of general formula [2a].

The coupling reaction may be practiced usually in an inert gas (for example, argon, nitrogen) atmosphere at 50 to $170°$ C. for $1$ minute to 24 hours. [Production Method 2] (2-a) The compound of general formula [7] can be obtained by reacting the compound of general formula [5] with an ortho ester such as methyl orthoformate or ethyl orthoformate in acetic anhydride and then with the compound of general formula [6]. The compound of general formula [5] can be producedby the method described in J. Med. Chem., Vol. 336, p.1580–1596, 1993, or a method similar thereto.

The solvent used in the reactions is not limited particularly as far as it does not adversely affect the reaction. It includes, for example, aromatic hydrocarbons such as benzene, toluene and xylene; ethers such as dioxane, tetrahydrofuran, anisole, diethylene glycol diethyl ether and dimethyl cellosolve; alcohols such as methanol, ethanol and propanol; halogenated hydrocarbons such as methylene chloride, chloroform and dichloroethane; amides such as N,N-dimethylformamide, N,N-dimethylacetamide and 1-methyl-2-pyrrolidone; and sulfoxides such as dimethyl sulfoxide, and the like. These solvents may be used in admixture.

In the reaction, the use amount of ortho ester may be equimolar or more, preferably 1 to 10 fold by mole, based on the compound of general formula [5].

The reaction may be practiced usually at 0 to 150° C., preferably 50 to 150° C., for 20 minutes to 50 hours.

In the subsequent reaction, the use amount of the compound of general formula [6] may be equimolar amount or more based on the compound of general formula [5], and the reaction may be practiced usually at 0 to 100° C., preferably 10 to 60° C., for 20 minutes to 30 hours. (2-b) As an alternative method, the compound of general formula [7] can be obtained by reacting the compound of general formula [5] with an acetal such as N,N-dimethylformamide dimethyl acetal or N,N-dimethylformamide diethyl acetal in the presence or absence of acid anhydride such as acetic anhydride and then with the compound of general formula [6].

The solvent used in these reactions is not particularly limited as far as it does not adversely affect the reactions. Specifically, it includes the same solvents as described in (2-a) above.

The use amount of acetal may be equimolar or more, preferably 1 to 5 fold by mole, based on the compound of general formula [5].

The use amount of acid anhydride may be equimolar or more, preferably 1 to 10 fold by mole, based on the compound of general formula [5].

The reaction may be practiced usually at 0 to 100° C., preferably 20 to 85° C., for 20 minutes to 50 hours.

In the subsequent reaction, the use amount of the compound of general formula [6] may be equimolar or more based on the compound of general formula [5] and the reaction may be practiced usually at 0 to 100° C., preferably 10 to 60° C., for 20 minutes to 30 hours. (2-c) The compounds of general formula [1a] can be obtained by subjecting the compounds of general formula [7] to cyclization reaction in the presence or absence of a fluoride salt or a base.

The solvent used in the reactions is not limited particularly as far as it does not adversely affect the reaction. It includes, for example, N,N-dimethylformamide, N,N-dimethylacetamide and 1-methyl-2-pyrrolidone; ethers such as dioxane, anisole, diethylene glycol diethyl ether and dimethyl cellosolve; and sulfoxides such as dimethyl sulfoxide, and the like. These solvents may be used in admixture.

The fluoride salt optionally used in the reaction includes, for example, sodium fluoride and potassium fluoride, and the like. The optionally used base includes, for example, sodium hydrogen carbonate, potassium carbonate, potassium tert-butoxide and sodium hydride, and the like.

The use amounts of fluoride salt and base each may be equimolar or more, preferably 1.0 to 3.0 fold by moles, based on the compound of general formula [7].

The reaction may be practiced usually at 0 to 180° C. for 5 minutes to 30 hours. [Production Method 3] (3-a) The compounds of general formula [10] can be obtained by reacting the compound of general formula [8] with the compound of general formula [9] in which Y represents a halogen atom in the presence of a base or by reacting the compound of general formula (8) with the compound of general formula (9) in which Y represents a trialkylsilyloxy group in the presence of an acid.

The solvent used in the reactions is not particularly limited as far as it does not adversely affect the reactions. When Y is a halogen atom, the solvent includes, for example, halogenated hydrocarbons such as methylene chloride, chloroform and dichloroethane; and aliphatic hydrocarbons such as pentane and hexane.

When Y is a trialkylsilyloxy group, the solvent includes, for example, alcohols such as methanol, ethanol, n-propanol, isopropanol, n-butanol, isobutanol, tert-butanol, n-hexanol and cyclopropanol.

The base used in the reaction includes, for example, trialkylamines such as triethylamine.

The acid used in the reaction includes, for example, organic acids such as formic acid, acetic acid, propionic acid, butyric acid, benzoic acid, toluylic acid, phthalic acid, methanesulfonic acid, benzenesulfonic acid and toluenensulfonic acid; and inorganic acids such as hydrochloric acid, sulfuric acid and phosphoric acid.

The use amount of base may be equimolar or more, preferably 1 to 5 fold by mole, based on the compound of general formula [8].

The use amount of acid may be 0.005 to 50 fold by mole or more, preferably 0.1 to 20 fold by mole, based on the compound of general formula [8].

The use amount of the compound of general formula [9] may be 1.0 to 2.0 folds by mole, preferably 1.0 to 1.3 folds by mole, based on the compound of general formula [8].

The reactions may be practiced usually in an inert gas (for example, argon, nitrogen) atmosphere at −20 to 100° C., preferably 20 to 90° C., for 0.5 to 24 hours.

The compounds of general formula [10] can be used in the subsequent reaction without isolation.

The compounds of general formula [9] can be produced by the methods described in Organic Synthesis, Vol. 63, p. 147, 1985, J. Chem. Soc., Chem. Commun., p. 897, 1987, etc. or methods similar thereto. (3-b) The compounds of general formula [11] can be obtained by subjecting the compounds of general formula [10] to reduction reaction.

The solvent used in the reaction is not limited particularly as far as it does not adversely affect the reaction. It includes, for example, ethers such as tetrahydrofuran, diethyl ether, dioxane, 1,2-diemthoxyethane, diethylene glycol dimethyl ether, triethylene glycol dimethyl ether and tetraethylene glycol dimethyl ether; aromatic hydrocarbons such as benzene, toluene and xylene; alcohols such as methanol, ethanol and isopropanol, and the like. These solvents may be used in admixture.

The reducing agent used in the reaction includes, for example, sodium borohydride in the presence of boron trifluoride, such as boron trifluoride ether complex or boron trifluoride tetrahydrofuran complex; sodium borohydride in the presence of a metal halide compound; sodium borohydride; aluminohydride complexes such as lithium aluminohydride, and the like.

The metal halide compound used in the reduction reaction includes aluminum chloride, iron (III) chloride, zinc chloride, cobalt (II) chloride, platinum (II) chloride, ruthenium (II) chloride, rhodium (II) chloride, palladium (II) chloride, zirconium (IV) chloride, calcium chloride and lithium chloride, and the like.

As the reduction reaction, catalytic reduction using metallic palladium such as palladium-activated carbon may be performed.

The use amount of the reducing agent may vary depending on the type of the reducing agent. For example, in the case of sodium borohydride, it is equimolar or more, preferably 1.0 to 2.5 fold by mole based on the compound of general formula [10].

The use amounts of boron trifluoride ether complex and boron trifluoride tetrahydrofuran complex are equimolar or more, preferably 1.3 to 3.3 fold by mole based on the compound of general formula [10].

The reaction may be practiced usually at −20 to 100° C., preferably at −5 to 80° C., for 2 to 10 hours. (3-c) The compounds of general formula [13] can be obtained by reacting the compounds of general formula [11] with the compounds of general formula [12] in the presence or absence of solvents.

The solvent which is optionally used in the reaction is not particularly limited as far as it does not adversely affect the reaction. It includes, for example, aromatic hydrocarbons such as benzene, toluene and xylene; ethers such as dioxane, tetrahydrofuran, anisole, diethylene glycol diethyl ether and dimethyl cellosolve; halogenated hydrocarbons such as methylene chloride, chloroform and dichloroethane; amides such as N,N-dimethylformamide, N,N-dimethylacetamide and 1-methyl-2-pyrrolidone; and sulfoxides such as dimethyl sulfoxide, and the like. These may be used in admixture.

The use amount of the compound of general formula [12] may be equimolar or more, preferably 1 to 10 fold by mole, based on the compound of general formula [11].

The reaction may be practiced preferably at 50 to 150° C. for 20 minutes to 50 hours.

The compounds of general formula [13] or salts thereof can be used in the subsequent reaction without isolation. (3-d) The compounds of general formula [1b] or salts thereof can be obtained by subjecting the compounds of general formula [13] to cyclization reaction in the presence or absence of solvents.

The cyclization reaction may be performed by heating in the presence or absence of cyclizing agents.

The cyclizing agent used in the reaction includes, for example, polyphosphoric acid, polyphosphoric acid esters, phosphorus pentoxide, concentrated sulfuric acid and the like cyclizing agents.

When the heating is performed in the absence of cyclizing agents, the optionally used solvent is not particularly limited as far as it does not adversely affect the reaction. It includes, for example, high boiling inert solvents such as biphenyl, diphenyl ether, o-dichlorobenzene and dibutyl phthalate. These may be used in admixture. The reaction may be practiced usually at 50 to 260° C. for 1 minute to 50 hours, preferably at 100 to 260° C. for 10 minutes to 3 hours.

The solvent which is optionally used upon heating in the presence of cyclizing agents is not particularly limited as far as it does not adversely affect the reaction. It includes, for example, benzene, dioxane and dimethylformamide when polyphosphoric acid, a polyphosphoric acid ester, phosphorus pentoxide or the like is used as a cyclizing agent. When concentrated sulfuric acid is used as a cyclizing agent, the solvent includes acetic anhydride and acetic acid. The solvents may be used in admixture.

The use amount of cyclizing agent may be equimolar amount or more, preferably 1 to 10 folds by mole, based on the compound of general formula [13].

The reaction may be practiced usually at 50 to 260° C. for 1 minute to 50 hours, preferably at 50 to 140° C. for 10 minutes to 3 hours.

The compounds of general formulae [1], [1a] and [1b] thus obtained can be subjected to a reaction known per se, such as oxidation, reduction, rearrangement, substitution, halogenation, dehydration or hydrolysis, or suitable combinations thereof, so that they can be derived to other compounds of general formula [1].

The compounds of general formula [1] or salts thereof can be isolated and purified by conventional methods such as extraction, crystallization, and/or column chromatography.

Next, production methods of the compounds of general formulae [2a], [2b], [5] and [8], starting compounds for the production of the compounds of the present invention, will be explained.

The compounds of general formulae [2a] and [2b] can be produced by the methods described in International Publication No. WO96/05192 and Japanese Patent Application No. 8-47936 or methods similar thereto. Alternatively, they can be obtained by the following methods.

Production Method A

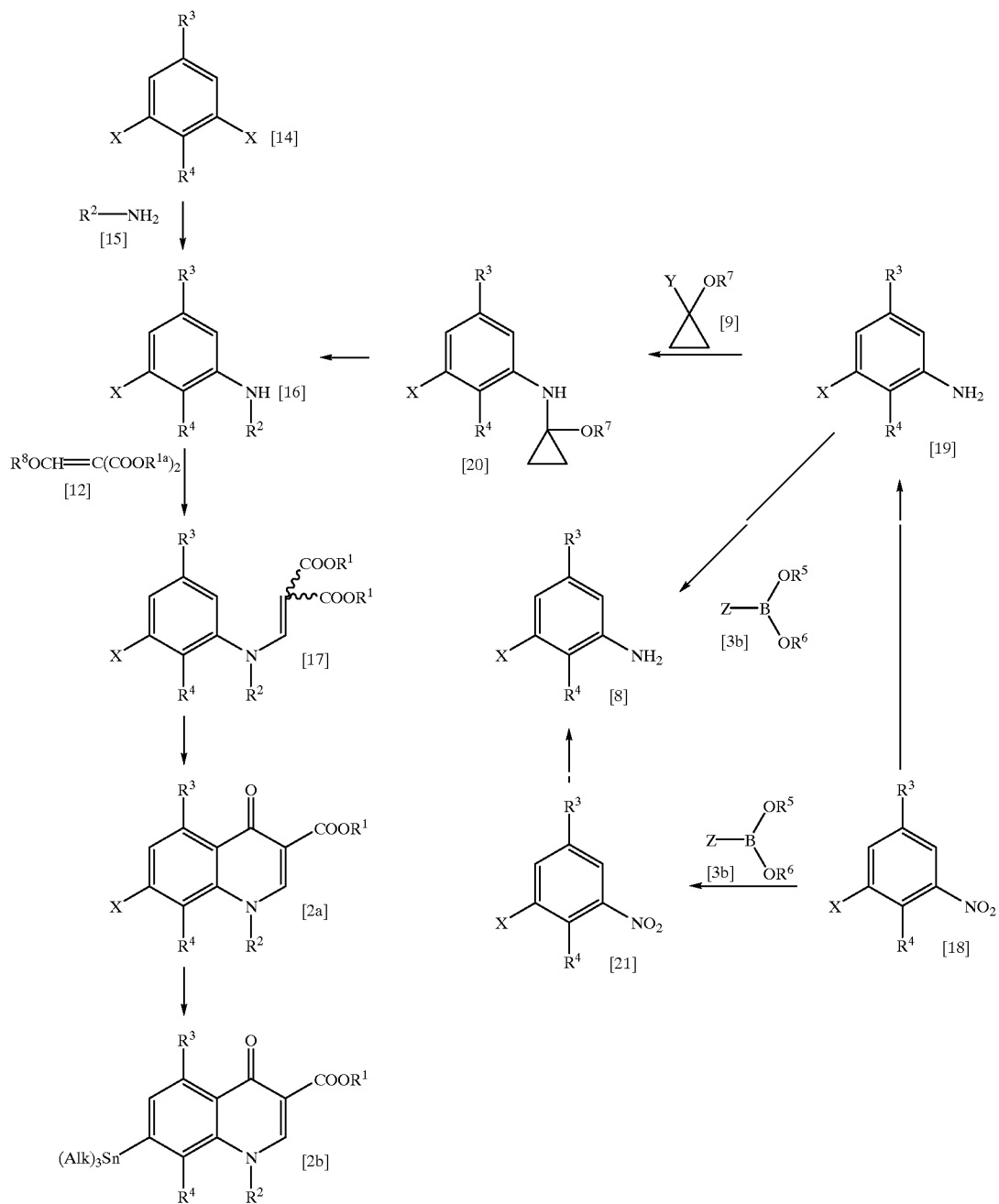

(In the formulae, $R^1$, $R^{1a}$, $R^2$, $R^3$, $R^4$ $R^5$, $R^6$, $R^7$, $R^8$, Alk, X, Y and Z have the same meanings as defined above.)

Production Method A

The compounds of general formula [16] can be produced from the compounds of general formula [14] according to the methods described in J. Am. Chem. Soc., Vol. 118, p. 7215–7216, 1996, J. Am. Chem. Soc., Vol. 118, p. 7217–7218, 1996, Tetrahedron Letters, Vol. 37, p. 4463–4466, 1996, Tetrahedron Letters, Vol. 38, p. 2073–2074, 1997, Tetrahedron Letters, Vol. 36, p. 3609–3612, 1995, J. Org. Chem., Vol. 61, p. 1133–1135, 1996 or methods similar thereto. More specifically, they can be produced, for example, by the following method.

The compounds of general formula [16] can be obtained by subjecting the compounds of general formula [14] and the compounds of general formula [15] to coupling reaction in the presence of a palladium catalyst, a base and a ligand.

The solvent which is optionally used in the reaction is not particularly limited as far as it does not adversely affect the reaction. It includes, for example, aromatic hydrocarbons such as benzene, toluene and xylene; ethers such as dioxane, tetrahydrofuran, anisole, diethylene glycol diethyl ether and dimethyl cellosolve; nitriles such as acetonitrile; amides such as N,N-dimethylformamide, N,N-dimethylacetamide and 1-methyl-2-pyrrolidone; and sulfoxides such as dimethyl sulfoxide, and the like. These may be used in admixture.

The palladium catalyst used in the reaction includes, for example, metallic palladium such as palladium-activated carbon and palladium black; inorganic palladium salts such as palladium chloride; organic palladium salts such as palladium acetate; and organic palladium complexes such as tetrakis(triphenylphosphine)palladium (0), bis(triphenylphosphine)palladium (II) chloride, bis(tricyclohexylphosphine)palladium (II) chloride and 1,1'-bis(diphenylphosphino)ferrocene palladium (II) chloride, and the like.

The use amount of palladium catalyst may be 0.00001 fold by mole or more, preferably 0.001 to 0.05 fold by mole, based on the compound of general formula [14].

The base used in the reaction includes, for example, potassium tert-butoxide, sodium tert-butoxide, sodium hydrogen carbonate, sodium carbonate, potassium carbonate, triethylamine, and the like.

The use amount of the base may be equimolar or more, preferably 2 to 5 fold by mole, based on the compound of general formula [14].

The ligand used in the reaction includes, for example, 2,2'-bis(diphenylphosphino)-1,1'-binaphthyl, tri-(orthotolyl) phosphine, 1,2-bis(diphenylphosphino)ethane, 1,2-bis(diphenylphosphino)propane, 1,2-bis(diphenylphosphino)benzene, 1,2-bis(diphenylphosphino)ethylene and 1,1'-bis(diphenylphosphino)ferrocene, and the like.

The use amount of the ligand in the reaction may be 0.00001 fold by mole or more, preferably 0.001 to 0.05 fold by mole, based on the compound of general formula [14].

The use amount of the compound of general formula [15] may be equimolar or more, preferably 1.0 to 1.5 fold by mole, based on the compound of the formula [14].

The coupling reaction may be practiced usually in an inert gas (for example, argon, nitrogen) atmosphere at 50 to 170° C. for 1 minute to 24 hours.

As an alternative method, the compounds of general formula [16] can be produced by subjecting the compounds of general formula [20] to reduction reaction.

The solvent used in the reaction is not limited particularly as far as it does not adversely affect the reaction. It includes, for example, alcohols such as methanol, ethanol and isopropanol; ethers such as diethyl ether, tetrahydrofuran, dioxane, 1,2-dimethoxyethane and diethylene glycol dimethyl ether; nitriles such as acetonitrile; amides such as N,N-dimethylformamide, N,N-dimethylacetamide and 1-methyl-2-pyrrolidone; sulfoxides such as dimethyl sulfoxide; aromatic hydrocarbons such as benzene, toluene and xylene; and water, and the like. These may be used in admixture.

The reducing agent used in the reaction includes, for example, alkali metals such as lithium, sodium and potassium; alkaline earth metals such as magnesium and calcium; zinc; metal salts such as aluminum, chromium, titanium, iron, cobalt, platinum, rhodium, palladium, ruthenium, samarium and selenium hydrosulfite sodium salts; metal hydrides such as diisobutylaluminum hydride, trialkylaluminum hydride, tin hydride compounds and hydrosilane; borohydride complexes such as sodium borohydride, lithium borohydride, potassium borohydride and calcium borohydride; aluminohydride complexes such as lithium aluminohydride; and boranes and alkylboranes, and the like.

The use amount of the reducing agent used in the reaction may vary depending on the type of the reducing agent. For example, in the case of borohydride complexes, it is 0.25 fold by mole or more, preferably 1.0 to 2.0 folds by mole, based on the compound of general formula [20].

The reduction reaction may be practiced usually at −20 to 120° C., preferably 0 to 80° C., for 10 minutes to 24 hours.

The compounds of general formula [20] can be obtained by subjecting the compounds of general formula [18] to ordinary reduction reaction to convert them to the compounds of general formula [19] and then reacting the compounds of general formula [19] with the compounds of general formula [9] in the presence of acids.

The solvent used in the reaction includes alcohols such as methanol, ethanol, n-propanol, isopropanol, n-butanol, isobutanol, tert-butanol, n-hexanol, cyclopentanol and cyclohexanol. These may be used in admixture.

The acid which is used in the reaction includes, for example, organic acids such as aliphatic carboxylic acids, e.g., formic acid, acetic acid, propionic acid and butyric acid; aromatic carboxylic acids, e.g., benzoic acid, toluylic acid and phthalic acid; aliphatic sulfonic acids, e.g., methanesulfonic acid; aromatic sulfonic acids, e.g., benzenesulfonic acid and toluenesulfonic acid and inorganic acids such as hydrochloric acid, sulfuric acid and phosphoric acid.

The use amount of acid may be 0.005 fold by mole or more, preferably 0.1 to 20 fold by mole, based on the compound of general formula [19].

The use amount of the compound of general formula [9] may be equimolar or more, preferably 1.0 to 1.3 fold by mole, based on the compound of general formula [19].

The reaction may be practiced usually at 0 to 120° C., preferably 20 to 100° C., for 10 minutes to 24 hours.

The compounds of general formula [17] can be obtained by reacting the compounds of general formula [16] with the compounds of general formula [12], for example, alkoxymethylenemalonic acid dialkyl esters such as diethyl ethoxymethylenemalonate in the presence or absence of solvents.

The solvent optionally used in the reaction is not particularly limited as far as it does not adversely affect the reaction. It includes, for example, aromatic hydrocarbons such as benzene, toluene and xylene; ethers such as dioxane, tetrahydrofuran, anisole, diethylene glycol diethyl ether and dimethyl cellosolve; halogenated hydrocarbons such as methylene chloride, chloroform and dichloroethane; amides such as N,N-dimethylformamide, N,N-dimethylacetamide and 1-methyl-2-pyrrolidone; and sulfoxides such as dimethyl sulfoxide, and the like. These solvents may be used in admixture.

The use amount of alkoxymethylenemalonic acid dialkyl esters maybe equimolar or more, preferably 1 to 10 fold by mole, based on the compound of general formula [16].

The reaction may be practiced preferably at 50 to 150° C. for 20 minutes to 50 hours.

The compounds of general formula [17] may be used in the subsequent reaction without isolation. (A-a) The compounds of general formula [2a] can be obtained by subjecting the compounds of general formula [17] to heating reaction in the presence or absence of solvents.

The solvent which is optionally used in the reaction is not particularly limited as far as it does not adversely affect the reaction. It includes, for example, high boiling inert solvents such as biphenyl, diphenyl ether, orthodichlorobenzene and dibutyl phthalate. These may be used in admixture.

The reaction may be practiced usually at 50 to 260° C. for 1 minute to 50 hours, preferably at 100 to 260° C. for 10 minutes to 3 hours. (A-b) The compounds of general formula [2a] can be obtained by subjecting the compounds of general formula [17] to heating reaction in the presence of a cyclizing agent and in the presence or absence of solvents.

The cyclizing agent used in the reaction includes, for example, polyphosphoric acid, polyphosphoric acid esters, phosphorus pentoxide, concentrated sulfuric acid and the like cyclizing agents.

The solvent optionally used in the reaction is not particularly limited as far as it does not adversely affect the reaction. In addition to the solvents exemplified in (A-a) above, it includes, for example, benzene, dioxane and dimethylformamide when polyphosphoric acid, a polyphosphoric acid ester, phosphorus pentoxide or the like is used as a cyclizing agent. When concentrated sulfuric acid is used as a cyclizing agent, the solvent includes acetic anhydride and acetic acid. The solvents to be used may be used in admixture.

The use amount of cyclizing agent may be equimolar or more, preferably 1 to 10 fold by mole, based on the compound of general formula [17].

The reaction may be practiced usually at 50 to 260° C. for 1 minute to 50 hours, preferably at 50 to 140° C. for 10 minutes to 3 hours.

In the reaction, hydrolysis reaction of ester groups proceeds simultaneously, so that among the compounds of general formula [2a], those compounds in which $R^1$ is a hydrogen atom can also be obtained directly.

The compounds of general formula [2b] can be obtained by subjecting the compounds of general formula [2a] and hexaalkyldistannan to coupling reaction using a palladium catalyst.

The hexaalkyldistannan includes hexabutyldistannan.

The solvent used in the reaction is not limited particularly as far as it does not adversely affect the reaction. It includes, for example, aromatic hydrocarbons such as benzene, toluene and xylene; ethers such as dioxane, tetrahydrofuran, anisole, diethylene glycol diethyl ether and dimethyl cellosolve; nitrites such as acetonitrile; amides such as N,N-dimethylformamide, N,N-dimethylacetamide and 1-methyl-2-pyrrolidone; and sulfoxides such as dimethyl sulfoxide, and the like. These solvents may be used in admixture.

The palladium catalyst used in the reaction includes, for example, metallic palladium such as palladium-activated carbon and palladium black; inorganic palladium salts such as palladium chloride; organic palladium salts such as palladium acetate; and organic palladium complexes such as tetrakis(triphenylphosphine)palladium (0), bis (triphenylphosphine)palladium (II) chloride, bis (tricyclohexylphosphine)palladium (II) chloride and 1,1'-bis (diphenyl-phosphino)ferrocene palladium (II) chloride, and the like.

The use amount of palladium catalyst may be 0.00001 fold by mole or more, preferably 0.001 to 0.05 fold by mole, based on the compound of general formula [2a].

The use amount of hexaalkyldistannan may be equimolar or more, preferably 1.0 to 3.0 fold by mole, based on the compound of general formula [2a].

The coupling reaction maybe practiced usually in an inert gas (for example, argon, nitrogen) atmosphere at 50 to 170° C. for 1 minute to 24 hours. (A-c) The compounds of general formula [21] can be obtained by subjecting the compounds of general formula [18] and the compound of general formula [3b] in the presence or absence of bases using a palladium catalyst.

The solvent used in the reaction is not particularly limited as far as it does not adversely affect the reaction. It includes, for example, water; alcohols such as methanol, ethanol and propanol; aromatic hydrocarbons such as benzene, toluene and xylene; halogenated hydrocarbons such as methylene chloride, chloroform and dichloroethane; ethers such as dioxane, tetrahydrofuran, anisole, 1,2-dimethoxyethane, diethylene glycol diethyl ether and dimethyl cellosolve; esters such as ethyl acetate and butyl acetate; ketones such as acetone and methyl ethyl ketone; nitriles such as acetonitrile; amides such as N,N-dimethylformamide, N,N-dimethylacetamide and 1-methyl-2-pyrrolidone; and sulfoxides such as dimethyl sulfoxide, and the like. These may be used in admixture.

The base optionally used in the reaction includes, for example, sodium hydrogen carbonate, sodium carbonate, potassium carbonate, tripotassiumphosphate, cesium carbonate, cesium fluoride, potassium fluoride, sodium fluoride and triethylamine.

The palladium catalyst used in the reaction includes, for example, metallic palladium such as palladium-activated carbon and palladium black; inorganic palladium salts such as palladium chloride; organic palladium salts such as palladium acetate; and organic palladium complexes such as tetrakis(triphenylphosphine)palladium (0), bis (triphenylphosphine)palladium (II) chloride, bis (tricyclohexylphosphine)palladium (II) chloride and 1,1'-bis (diphenylphosphino)ferrocene palladium (II) chloride, and the like.

The use amount of the base used in the reaction may be equimolar or more, preferably 2 to 5 fold by mole, based on the compound of general formula [18].

The use amount of the palladium catalyst may be 0.00001 fold by mole or more, preferably 0.001 to 0.005 fold by mole, based on the compound of general formula [18].

The use amount of the compound of general formula [3b] may be equimolar or more, preferably 1.0 to 1.5 fold by mole, based on the compound of general formula [18].

The coupling reaction may be practiced usually in an inert gas (for example, argon, nitrogen) atmosphere at 50 to 170° C. for 1 minute to 24 hours. (A-d) The compounds of general formula [8] can be produced by subjecting the compounds of general formula [21] to reduction reaction.

The solvent used in the reaction is not particularly limited as far as it does not adversely affect the reaction. It includes, for example, alcohols such as methanol, ethanol and isopropanol; ethers such as tetrahydrofuran, dioxane, 1,2-dimethoxyethane and diethylene glycol diethyl; nitrites such as acetonitrile; amides such as N,N-dimethylformamide, N,N-dimethylacetamide and 1-methyl-2-pyrrolidone; sulfoxides such as dimethyl sulfoxide; and water, and the like. These may be used in admixture.

The reducing agent used in the reaction includes, for example, metals such as zinc, aluminum, iron and tin and salts thereof; borohydride complexes such as sodium borohydride, lithium borohydride, potassium borohydride and calcium borohydride, and the like. When iron is used as a reducing agent, ammonium chloride may be used as a reaction promoter.

As the reduction reaction, catalytic reduction using metallic palladium such as palladium-activated carbon may be carried out.

The use amount of the reducing agent used in the reaction may vary depending on the type of the reducing agent. It is equimolar or more, preferably 1 to 5 fold by mole, based on the compound of general formula [21].

The use amount of the reaction promoter may be equimolar, preferably 0.1 to 3 fold by mole, based on the compound of general formula [21].

The reaction may be practiced usually at −20 to 150° C., preferably 0 to 100° C., for 10 minutes to 24 hours. (A-e) The compounds of general formula [8] can be obtained by subjecting the compound of general formula [19] and the compound of general formula [3b] to coupling reaction in the presence or absence of a base using a palladium catalyst or a nickel catalyst.

The solvent used in the reaction is not limited particularly as far as it does not adversely affect the reaction. It includes, for example, water; alcohols such as methanol, ethanol and propanol; aromatic hydrocarbons such as benzene, toluene and xylene; halogenated hydrocarbons such as methylene chloride, chloroform and dichloroethane; ethers such as 1,2-dimethoxyethane, dioxane, tetrahydrofuran, anisole, diethylene glycol diethyl ether and dimethyl cellosolve; esters such as ethyl acetate and butyl acetate; ketones such as acetone and methyl ethyl ketone; nitrites such as acetonitrile; amides such as N,N-dimethylformamide, N,N-dimethylacetamide and 1-methyl-2-pyrrolidone; and sulfoxides such as dimethyl sulfoxide, and the like. These may be used in admixture.

The base optionally used in the reaction includes, for example, sodium hydrogen carbonate, sodium carbonate, potassiumcarbonate, tripotassiumphosphate, cesiumcarbonate, cesium fluoride, potassium fluoride, sodium fluoride and triethylamine.

The palladium catalyst used in the reaction includes, for example, organic palladium salts such as palladium acetate; and organic palladium complexes such as tetrakis (triphenylphosphine)palladium (0), bis(triphenylphosphine) palladium (II) chloride, bis(tricyclohexylphosphine) palladium (II) chloride and 1,1'-bis (diphenylphosphino) ferrocene palladium (II) chloride, and the like.

The nickel catalyst used in the reaction includes, for example, organic nickel complexes such as bis (diphenylphosphino)ethane nickel (II) chloride, bis (diphenylphosphino)propane nickel (II) chloride, bis (diphenylphosphino)butane nickel (II) chloride, bis (triphenylphosphine) nickel (II) chloride and 1,1'-bis (diphenylphosphino)ferrocene nickel (II) chloride.

The use amount of the base may be equimolar or more, preferably 2 to 5 fold by mole, based on the compound of general formula [19].

The use amount of the palladium catalyst or nickel catalyst may be 0.00001 fold by mole or more, preferably 0.001 to 0.05 fold by mole, based on the compound of general formula [19].

The use amount of the compound of general formula [3b] may be equimolar or more, preferably 1.0 to 1.5 fold by mole, based on the compound of general formula [19].

The coupling reaction may be practiced usually in an inert gas (for example, argon, nitrogen) atmosphere at 50 to 170° C. for 1 minute to 24 hours.

The compounds of general formula [3b] can be produced by subjecting halogeno heterocyclic rings to boration reaction.

The reaction may be practiced by the methods described in Jikken Kagaku Koza, 4th edition, Vol. 24, p. 61–91, 1992 and J. Org. Chem., Vol. 58, p. 201–2208, 1993 and methods similar thereto.

The compounds of general formulae [3a] and [4] can be produced by the methods described in Dai Yuki Kagaku 16 [III], 1 (1969), Shin Jikken Kagaku Koza, 14 [IV], p. 2056 (1978), etc. and methods similar thereto.

In the production methods described above, the compounds of general formulae [1a], [2a], [2b], [3a], [3b], [4], [5], [7], [8], [10], [11], [13], [14], [15], [16], [17], [18], [19], [20] and [21] may be used in the form of their salts. The salts include the same salts as those explained as the salts of the compounds of general formula [1].

In the production methods described above, the compounds of general formulae [2a], [2b], [3a], [3b], [4], [5], [6], [7], [8], [9], [10], [11], [12], [13], [14], [15], [16], [17], [18], [19], [20] and [21] maybe isomers (for example, optical isomers, geometrical isomers and tautomers) if such exist. Also, solvates, hydrates and various forms of crystals thereof may also be used.

Among the compounds of the formulae formulae [1a], [1b], [2a], [2b], [3a], [3b], [4], [5], [6], [7], [8], [9], [10], [11], [12], [13], [14], [15], [16], [17], [18], [19], [20] and [21], those compounds having an amino group, a hydroxyl group or a carboxyl group may be protected in advance with an ordinary protective group, which is then eliminated after the reaction by a method known per se.

When the compounds of the present invention are used as medicines, they may be mixed with pharmaceutical ingredient conventionally used in formulating pharmaceutical preparations, such as excipients, carriers and diluents. They may be administered by oral or parenteral administration in the form of tablets, capsules, powder, syrup, granules, pills, suspensions, emulsions, liquids, powdery preparations, suppositories, eye drops, nasal drops, ear drops, dressings, ointments, or injections in accordance with the conventional method. Preferably, they may be prepared as parenteral drugs, particularly drugs for application to mucosa or topical preparations. The administration method, dose and number of times of administration can be selected appropriately depending on the age, weight and symptom of patients. Usually, the compounds of the present invention may be administered to adults at a dose of 0.1 to 100 mg/kg at a time or in several times in portions by oral or parenteral administration (for example, injection, drip infusion and administration to rectal portion. Preferably, they may be administered at the same dose as above by parenteral administration, for example, application to mucosa or topical administration to the skin.

Next, the pharmacological activities of typical compounds of the present invention will be explained.

Test Compounds a: 1-Cyclopropyl-7-(2,6-dimethyl-4-pyridyl)-8-methyl-4-oxo-1,4-dihydro-3-quinolinecarboxylic acid
b: 1-Cyclopropyl-7-(2-hydroxymethyl-6-methyl-4-pyridyl)-8-methyl-4-oxo-1,4-dihydro-3-quinolinecarboxylic acid
c: 1-Cyclopropyl-7-(6-methyl-3-pyridyl)-8-methyl-4-oxo-1,4-dihydro-3-quinolinecarboxylic acid
d: 1-Cyclopropyl-8-methyl-7-[5-methyl-6-(methylamino)-3-pyridyl]-4-oxo-1,4-dihydro-3-quinolinecarboxylic acid
e: 7-(6-Amino-5-methyl-3-pyridyl)-1-cyclopropyl-8-(difluoromethoxy)-4-oxo-1,4-dihydro-3-quinolinecarboxylic acid
f: 7-(6-Amino-5-methyl-3-pyridyl)-1-cyclopropyl-8-methoxy- 4-oxo-1,4-dihydro-3-quinolinecarboxylic acid
g: 7-(6-Amino-5-methyl-3-pyridyl)-1-cyclopropyl-8-methyl-4-oxo-1,4-dihydro-3-quinolinecarboxylic acid
h: 7-(6-Amino-3-pyridyl)-1-cyclopropyl-8-methyl-4-oxo-1,4-dihydro-3-quinolinecarboxylic acid
i: 1-Cyclopropyl-7-(2,6-dimethyl-4-pyridyl)-5,8-dimethyl-4-oxo-1,4-dihydro-3-quinolinecarboxylic acid
j: 5-Amino-1-cyclopropyl-7-(5,6-dimethyl-3-pyridyl)-8-methyl-4-oxo-1,4-dihydro-3-quinolinecarboxylic acid
k: (Control): (±)-9-Fluoro-6,7-dihydro-8-(4-hydroxy-1-piperidinyl)-5-methyl-1-oxo-1-1H,5H-benzo[i,j]quinolizine-2-carboxylic acid [general name: nadifloxacin]

Antibacterial Activity

Test Method 1

The drug sensitivity of Propionibacterium acnes (P. acnes JCM6425) was assayed according to the standard method of Japan Chemotherapy Society [CHEMOTHERAPY, Vol. 41, No. 2, p. 183–189 (1993)]. More particularly, the test bacteria cells on the modified GAM agar [GAM agar, modified "Nissui"] (manufactured by Nissui Seiyaku) medium incubated at 35° C. for 2 days were suspended in modified GAM bouillon (GAM broth, modified "Nissui") [manufactured by Nissui Seiyaku] to 1 McFarand and the cell suspension was diluted 5 fold with the same medium to obtain a cell suspension for inoculation. The cell suspension was inoculated in the wells of a micro plate, each dispensed with 100 µl of modified GAM bouillon containing the drug in two-fold dilution series to a final cell density of $10^5$ CFU/well, and incubated in an anaerobic incubator (Forma Scientific anaerobic system: model 1024) at 35° C. for 2 days. MIC (µ/ml) was defined as the lowest concentration which inhibited visible growth of the cells. The results obtained are shown in Table 1.

TABLE 1

| a | b | c | d | e | f |
|---|---|---|---|---|---|
| 0.0156 | 0.0313 | 0.0313 | 0.0313 | 0.0625 | 0.0313 |
| g | h | i | j | k | |
| 0.0078 | 0.0156 | 0.0313 | 0.0156 | 0.25 | |

Test Method 2

Test Method

According to the standard method of Japan Chemotherapy Society [CHEMOTHERAPY, Vol. 29, No. 1, p. 76–79 (1981)], Staphylococcus aureus (S. aureus F-1924) was cultivated in Mueller Hinton broth [manufactured by Difco] at 37° C. for 20 hours and the cell density was adjusted to $10^6$ cells/plate ($10^8$ cells/ml). A loopful of the bacterial suspension was inoculated on Mueller Hinton agar medium [manufactured by Difco] and incubated at 37° C. for 20 hours. Whether or not the growth of cells occurred was observed and MIC (µg/ml) was defined as the lowest concentration which inhibited visible growth of the cells. The results obtained are shown in Table 2.

TABLE 2

| a | b | c | d | e | f |
|---|---|---|---|---|---|
| 0.2 | 0.39 | 0.39 | 0.2 | 0.78 | 0.39 |
| g | h | i | j | k | |
| 0.1 | 0.1 | 0.2 | 0.39 | 1.56 | |

Test Method 3

Micronucleus Test

According to the description in Dokusei Shiken Koza 12 (Chijinshokan, 1991), pages 147–153, micronucleus test was carried out using ddy male mice. As a result, the compounds (a), (c), (d) and (g) were negative when administered intraperitoneally at 500 mg/Kg.

Test Method 4

Acute Toxicity

Three ddy male mice were intraperitoneally administered with 500 mg/Kg of (a), (b), (d) or (g). In no case, the animals were dead.

BEST MODE FOR CARRYING OUT THE INVENTION

Next, the present invention will be explained by examples and reference examples. However, the present invention should not be construed as being limited thereto. All the mixing ratios of eluent were by volume. As the carrier in column chromatography, silica gel No. 7734 (Merck Corp.) was used.

Reference Example 1

To a solution of 12.24 g of 2,6-dibromotoluene in 120 ml of toluene were added 2.94 g of cyclopropylamine, 0.45 g of tris(dibenzylideneacetone)dipalladium, 0.91 g of (S)-(-)-2, 2'-bis(diphenylphosphino)-1,1'-binaphthyl and 6.12 g of sodium tert-butoxide in order. The resulting solution was stirred in an argon atmosphere at 80° C. for 1 hour. After cooling the reaction mixture, 210 ml of ice water and 60 ml of ethyl acetate were added thereto and the mixture was adjusted to pH 1 with 6 mol/ml hydrochloric acid, insoluble matter was filtered off, and an organic layer was separated. The obtained organic layer was washed with saturated saline and dried over anhydrous magnesium sulfate and then the solvent was evaporated under reduced pressure. Purification of the residue by silica gel column chromatography [hexane:toluene=2:1] afforded 9.31 g of pale yellow oil of N-cyclopropyl-3-bromo-2-methylaniline.

IR (neat) $cm^{-1}$: 3420; NMR (CDCl$_3$) δ: 0.4–0.9 (4H, m), 2.19 (3H, s), 2.3–2.6 (1H, m), 3.9–4.3 (1H, m), 6.7–7.2 (3H, brs).

Similarly, the following compounds are obtained.

N-Cyclopropyl-3-bromo-2,5-dimethylaniline

NMR (CDCl$_3$) δ: 0.4–0.9 (4H, m), 2.1–2.6 (7H, m), 3.9–4.3 (1H, brs), 6.7–6.9 (2H, brs).

3-Bromo-5-(cyclopropylamino)-4-methylbenzoic acid tert-butyl ester

NMR (CDCl$_3$) δ: 0.4–1.0 (4H, m), 1.59 (9H, s), 2.22 (3H, s), 2.3–2.7 (1H, m), 4.0–4.4 (1H, brs), 7.59 (2H, s).

Reference Example 2

A solution of 0.68 g of N-cyclopropyl-3-bromo-2-methylaniline in 0.65 g of diethyl ethoxymethylenemalonate was stirred at 130° C. for 4 hours. After evaporating ethanol generated, 4.07 g of polyphosphoric acid was added and stirred at 130° C. for 15 minutes. To the reaction mixture were added 20 ml of chloroform and 20 ml of water under ice cooling and an organic layer was separated. The separated organic layer was dried over anhydrous magnesium sulfate and the solvent was evaporated under reduced pressure. Purification of the, residue by silica gel column chromatography [toluene:ethyl acetate=4:1] afforded 0.47 g of pale yellow crystals of ethyl 7-bromo-1-cyclopropyl-8-methyl-4-oxo-1,4-dihydro-3-quinolinecarboxylate.

IR (KBr) $cm^{-1}$: 1683, 1636; NMR (CDCl$_3$) δ: 0.8–1.6 (7H, m), 2.86 (3H, s), 3.8–4.2 (1H, m), 4.39 (2H, q, J=7.2 Hz), 7.60 (1H, d, J=8.4 Hz), 8.16 (1H, d, J=8.4 Hz), 8.67 (1H, s). Melting point: 169–171° C.

Similarly, the following compound was obtained.

7-Bromo-1-cyclopropyl-5,8-dimethyl-4-oxo-1,4-hydro-3-quinolinecarboxylic acid ethyl ester IR (KBr) cm$^{-1}$: 1739; NMR (CDCl$_3$) δ: 0.6–1.5 (7H, m), 2.74 (3H, s), 2.81 (3H, s), 3.7–4.1 (1H, m), 4.38 (2H, q, J=7.1 Hz), 7.36 (1H, s), 8.56 (1H, s).

Reference Example 3

A mixture of 4.76 g of 3-bromo-5-(cyclopropylamino)-4-methylbenzoic acid tert-butyl ester and 4.7 g of diethyl ethoxymethylenemalonate was stirred at 130° C. for 8 hours. Evaporation of the generated ethanol under reduced pressure and subsequent purification by column chromatography [hexane:ethyl actate=4:1] afforded 5.09 g of brown oil of diethyl 2-{[3-bromo-5-(tert-butoxycarbonyl)cyclopropyl-2-methylanilino]methylene}malonate.

NMR (CDCl$_3$) δ: 0.6–0.9 (4H, m), 1.1–1.4 (6H, m), 1.59 (9H, s), 2.34 (3H, s), 3.1–3.3 (1H, m), 3.6–4.3 (4H, m), 7.6–7.7 (2H, m), 8.1–8.2 (1H, m).

Reference Example 4

To a solution of 5.09 g of diethyl 2-{[3-bromo-5-(tert-butoxycarbonyl)cyclopropyl-2-methylanilino]methylene}malonate in 50 ml of methylene chloride was added 50 ml of trifluoroacetic acid and stirred for 3 hours under ice cooling. Evaporation of the solvent from the reaction mixture under reduced pressure, addition of hexane and ethyl acetate, and filtration of solids afforded 3.57 g of brown solids of 3-bromo-5-{cyclopropyl[3-ethoxy-2-(ethoxycarbonyl)-3-oxo-1-propenyl]amino}-4-methylbenzoic acid.

IR (KBr) cm$^{-1}$: 1720, 1701, 1647, 1638; NMR (CDCl$_3$) δ: 0.7–0.9 (4H, m), 1.0–1.4 (6H, m), 2.37 (3H, s), 3.0–3.4 (1H, m), 3.6–4.4 (4H, m), 5.6–6.4 (1H, brs), 7.65 (1H, s), 7.77 (1H, d, J=1.5 Hz), 8.23 (1H, d, J=1.5 Hz).

Reference Example 5

To a solution of 3.56 g of 3-bromo-5-{cyclopropyl[3-ethoxy-2-(ethoxycarbonyl)-3-oxo-1-propenyl]amino}-4-methylbenzoic acid in 71 ml of acetone were added 0.98 g of triethylamine and 1.06 g of ethyl chlorocarbonate at −20° C. and stirred at −20° C. to −30° C. for 1 hour. Then, a solution of 1.58 g of sodium azide in 3.5 ml of water was added thereto. The reaction mixture was warmed to room temperature and 200 ml of ethyl acetate and 100 ml of water were added thereto. Separating the organic layer, washing it with saturated saline, drying it over anhydrous magnesium sulfate, and evaporation of the solvent under reduced pressure afforded 4.2 g of brown oil. The oil was dissolved in 42 ml of toluene and refluxed for 30 minutes. Thereafter, 0.96 g of benzyl alcohol was added and the mixture was refluxed for 1 hour. Evaporation of the solvent from the reaction mixture under reduced pressure, purification of the residue by column chromatography [hexane:ethyl acetate=2:1], and filtration of precipitates after addition of hexane afforded 3.59 g of white solids of 2-[(5-{[(benzyloxy) carbonyl]amino}-3-bromocyclopropyl-2-methylanilino)methylene] malonic acid diethyl ester.

IR (KBr) cm$^{-1}$: 3328, 1731, 1698, 1579; NMR (CDCl$_3$) δ: 0.5–0.9 (4H, m), 1.0–1.4 (6H, m), 2.22 (3H, s), 2.9–3.3 (1H, m), 3.5–4.3 (4H, m), 5.19 (2H, s), 6.9–7.0 (1H, brs), 7.0–7.1 (1H, brs), 7.39 (5H, s), 7.5–7.7 (1H, brs), 7.7–7.9 (1H, brs).

Reference Example 6

A solution of 1.50 g of 2-[(5-{-[(benzyloxy)carbonyl]-amino}-3-bromocyclopropyl-2-methylanilino)methylene] malonic acid diethyl ester and 15 g of a polyphosphate ester in 15 ml of chloro form was refluxed for 40 minutes. The reaction mixture was added to a mixed solvent consisting of 100 ml of ethyl acetate and 100 ml of water and an organic layer was separated. The obtained organic layer was washed with a saturated sodium bicarbonate solution and saturated saline in order and dried over anhydrous magnesium sulfate and the solvent was evaporated under reduced pressure. The obtained residue was purified by column chromatography [toluene:ethyl acetate=5:1]. Addition of hexane and diisopropyl ether and filtration of the precipitated crystals afforded 1.01 g of pale yellow crystals of 5-{[(benzyloxy)carbonyl]amino}-7-bromo-1-cyclopropyl-8-methyl-4-oxo-1,4-dihydro-3-quinolinecarboxylic acid ethyl ester.

IR (KBr) cm$^{-1}$: 1724, 1621; NMR (CDCl$_3$) δ: 0.7–1.7 (7H, m), 2.71 (3H, s), 3.8–4.1 (1H, m), 4.38 (2H, q, J=7.1 Hz), 5.20 (2H, s), 7.2–7.6 (6H, m), 8.6–8.8 (2H, m).

Reference Example 7

A suspension of 8.00 g of 5-bromo-2-chloro-3-methyl-pyridine in 80 ml of an aqueous 40% methylamine solution was stirred in a sealed vessel at an outer bath temperature of 180° C. for 4 hours. The reaction mixture was added to a mixed solvent consisting of ice water and ethyl acetate to separate an organic layer. The obtained organic layer was washed with water and with saturated saline in order and dried over anhydrous magnesium sulfate and the solvent was evaporated under reduced pressure. Addition of water to the obtained residue and filtration of crystals afforded 7.10 g of pale yellow crystals of N-(5-bromo-3-methyl-2-pyridyl)-N-methylamine.

IR (KBr) cm$^{-1}$: 3332; NMR (CDCl$_3$) δ: 2.05 (3H, s), 3.00 (3H, d, J=4.6 Hz), 4.0–4.4 (1H, brs), 7.29 (1H, d, J=2.1 Hz), 8.06 (1H, d, J=2.1 Hz)

Similarly, the following compound was obtained.

N-(5-Bromo-3-methyl-2-pyridyl)-N,N-dimethylamine

IR (neat) cm$^{-1}$: 2928; NMR (CDCl$_3$) δ: 2.19 (3H, s), 2.76 (6H, s), 7.38 (1H, d, J=2.4 Hz), 8.05 (1H, d, J=2.4 Hz).

Reference Example 8

To a solution of 7.00 g of N-(5-bromo-3-methyl-2-pyridyl)-N-methylamine in 35 ml of pyridine was added 21 ml of acetic anhydride and the mixture was refluxed for 2 hours. The reaction mixture was concentrated under reduced pressure. Addition of isopropyl ether to the obtained residue and filtration of solids afforded 7.60 g of colorless crystals of N1-(5-bromo-3-methyl-2-pyridyl)-N1-methylacetamide.

IR (KBr) cm$^{-1}$: 1668; NMR (CDCl$_3$) δ: 1.80 (3H, s), 2.28 (3H, s), 3.19 (3H, s), 7.38 (1H, d, J=2.2 Hz), 8.05 (1H, d, J=2.2 Hz)

Similarly, the following compound was obtained.

N1-(5-Bromo-2-pyridyl)-N1-methylacetamide

IR (KBr) cm$^{-1}$: 1655; NMR (CDCl$_3$) δ: 2.16 (3H, s), 3.39 (3H, s), 7.34 (1H, d, J=8.4 Hz), 7.84 (1H, dd, J=8.4, 2.6 Hz), 8.51 (1H, d, J=2.6 Hz).

Reference Example 9

A solution of 8.00 g of 5-bromo-2,3-dimethyl-1-pyridine N(Py)-oxide in 24 ml of acetic anhydride was stirred at 100° C. for 1 hour. The reaction mixture was concentrated under reduced pressure and a mixed solvent consisting of 100 ml of water and 100 ml of chloroform was added to the obtained residue. The mixture was adjusted to pH 8 with a saturated aqueous sodium bicarbonate solution and then an organic layer was separated. The separated organic layer was washed with water and with saturated saline in order and dried over anhydrous magnesium sulfate, followed by evaporation of the solvent under reduced pressure. Purification of the obtained residue by column chromatography [eluent; n-hexane:ethyl acetate=10:1] afforded 5.56 g of colorless oil of (5-bromo-3-methyl-2-pyridyl)methyl acetate.

IR (neat) cm$^{-1}$: 1742; NMR (CDCl$_3$) δ: 2.14 (3H, s), 2.36 (3H, s), 5.18 (2H, s), 7.66 (1H, d, J=1.8 Hz), 8.50 (1H, d, J=1.8 Hz).

Reference Example 10

To a solution of 5.50 g of (5-bromo-3-methyl-2-pyridyl) methyl acetate in 27 ml of ethanol was added 27 ml of an aqueous 1 mol/l sodium hydroxide solution and the mixture was stirred at room temperature for 1 hour. The reaction mixture was concentrated under reduced pressure, a mixed solvent consisting of 100 ml of water and 100 ml of chloroform was added to the obtained residue, and an organic layer was separated. The separated organic layer was washed with water and with saturated saline in order and dried over anhydrous magnesium sulfate. Evaporation of the solvent under reduced pressure afforded 4.17 g of pale yellow crystals of (5-bromo-3-methyl-2-pyridyl)methanol.

IR (KBr) cm$^{-1}$: 3442; NMR (CDCl$_3$) δ: 2.22 (3H, s), 4.3–4.9 (3H, m), 7.62 (1H, d, J=1.6 Hz), 8.45 (1H, d, J=1.6 Hz).

Reference Example 11

To a solution of 2.30 g of (5-bromo-3-methyl-2-pyridyl) methanol in 23 ml of methylene chloride was added 0.97 ml of thionyl chloride under ice cooling and the mixture was stirred for 30 minutes at the same temperature as above. The reaction mixture as concentrated under reduced pressure and the residue was suspended in 20 ml of methylene chloride. Under ice cooling 20 ml of an aqueous methylamine solution (40% w/w) was added. After stirring at room temperature for 5 hours, an organic layer was separated. The separated organic layer was washed with water and dried over anhydrous magnesium sulfate and the solvent was evaporated under reduced pressure. Purification of the obtained residue by column chromatography [eluent; chloroform:ethanol=10:1] afforded 1.25 g of N-[(5-bromo-3-methyl-2-pyridyl)methyl]-N-methylamine.

NMR (CDCl$_3$) δ: 2.30 (3H, s), 2.50 (3H, s), 3.78 (2H, s), 7.58 (1H, d, J=1.7 Hz), 8.43 (1H, d, J=1.7 Hz).

Reference Example 12

To a solution of 1.20 g of N-[(5-bromo-3-methyl-2-pyridyl) methyl]-N-methylamine in 6 ml of methylene chloride was added 0.93 ml of triethylamine under ice cooling. Thereafter, a solution of 0.88 ml of benzyloxycarbonyl chloride in 4 ml of methylene chloride was dropped thereto over 20 minutes. The mixture was stirred at the same temperature as above for 30 minutes and 10 ml of water was added thereto and an organic layer was separated. The separated organic layer was washed with water and dried over anhydrous magnesium sulfate and the solvent was evaporated under reduced pressure. Purification of the obtained residue by column chromatography [eluent; n-hexane:ethyl acetate=3:1] afforded 1.89 g of colorless oil of benzyl N-[(5-bromo-3-methyl-2-pyridyl)methyl]-N-methyl carbamate.

IR (neat) cm$^{-1}$: 1702; NMR (CDCl$_3$) δ: 2.28(3H, s), 2.94 (3H, s), 4.56(2H, s), 5.15 (2H, s), 7.1–7.4 (5H, m), 7.5–7.6 (1H, brs), 8.3–8.5(1H, brs).

Reference Example 13

A suspension of 0.50 g of 2,5-dibromopyridine in 2 ml of methylhydrazine was refluxed under a nitrogen atmosphere for 5 hours. After cooling it to room temperature, the reaction mixture was added to a mixed solvent consisting of 20 ml of water and 20 ml of ethyl acetate and an organic layer was separated. The separated organic layer was washed with water and with saturated saline in order and dried over anhydrous magnesium sulfate and the solvent was evaporated under reduced pressure. Purification of the obtained residue by column chromatography [eluent; toluene:ethyl acetate=5:1] afforded 0.38 g of pale yellow crystals of 1-(5-bromo-2-pyridyl)-2-methylhydrazine.

IR (KBr) cm$^{-1}$: 3296; NMR (CDCl$_3$) δ: 3.25 (3H, s), 3.5–4.3 (2H, m), 6.91 (1H, d, J=9.0 Hz), 7.52 (1H, dd, J=9.0, 2.4 Hz), 8.13 (1H, d, J=2.4 Hz).

Reference Example 14

To a solution of 0.35 g of 1-(5-bromo-2-pyridyl)-2-methylhydrazine in 3 ml of pyridine was added 1.3 ml of acetic anhydride and the mixture was refluxed for 4 hours. After cooling it to room temperature, the reaction mixture was concentrated under reduced pressure. To the obtained residue was added a mixed solvent consisting of 20 ml of water and 20 ml of ethyl acetate and the mixture was adjusted to pH 8 with a saturated aqueous sodium bicarbonate solution. Thereafter, an organic layer was separated. The separated organic layer was washed with water and with saturated saline in order and dried over anhydrous magnesium sulfate and the solvent was evaporated under reduced pressure. Purification of the obtained residue by column chromatography [eluent; n-hexane:ethyl acetate=5:1] afforded 0.47 g of colorless crystals of N'1-acetyl-N1-(5-bromo-2-pyridyl)-N'1-methylethano-hydrazide.

IR (KBr) cm$^{-1}$: 1711; NMR (CDCl$_3$) δ: 2.40 (6H, s), 3.32 (3H, s), 6.45 (1H, d, J=8.9 Hz), 7.62 (1H, dd, J=8.9, 2.3 Hz), 8.24 (1H, d, J=2.3 Hz).

Reference Example 15

Under a nitrogen atmosphere, 19.5 g of N1-(5-bromo-3-methyl-2-pyridyl)-N1-methylacetamide, 93.1 g of hexabutyldistannan and 2.25 g of bis(triphenylphosphine)palladium (II) chloride were added to 190 ml of toluene and the mixture was refluxed for 3 hours. Evaporation of the solvent under reduced pressure and purification of the obtained residue by column chromatography [eluent; hexane:ethyl acetate=3:1 ] afforded 15.0 g of colorless oil of N1-methyl-N1-[3-methyl-5-(1,1,1-tributylstannyl)-2-pyridyl] acetamide.

IR (neat) cm$^{-1}$: 2927, 1673; NMR (CDCl$_3$) δ: 0.4–2.0 (30H, m), 2.25 (3H, s), 3.21 (3H, s), 7.6–7.8 (1H, brs), 8.2–8.5 (1H, brs).

Similarly, the following compounds were obtained.
2-Methoxy-5-(1,1,1-tributylstannyl)pyridine IR (neat) cm$^{-1}$: 2928; NMR (CDCl$_3$) δ: 0.4–2.0 (27H, m), 3.93 (3H, s), 6.74 (1H, d, J=8.1 Hz), 7.61 (1H, dd, J=1.7 Hz, 8.1 Hz), 8.16 (1H, d, J=1.7 Hz).
N1-[3-Methyl-5-(1,1,1-tributylstannyl)-2-pyridyl]-acetamide IR (neat) cm$^{-1}$: 2927, 1676; NMR (CDCl$_3$) δ: 0.6–2.0 (27H, m), 2.24 (3H, s), 2.26 (3H, s), 7.6–7.7 (1H, brs), 8.2–8.3 (1H, brs), 8.7–9.0 (1H, brs).
N,N-Dimethyl-N-[3-methyl-5-(1,1,1-tributylstannyl)-2-pyridyl]amine IR (neat) cm$^{-1}$: 2927; NMR (CDCl$_3$) δ: 0.4–2.0 (27H, m), 2.28 (3H, s), 2.86 (6H, s), 7.4–7.5 (1H, brs), 8.1–8.2 (1H, brs).

N1-Methyl-N1-[5-(1,1,1-tributylstannyl)-2-pyridyl]-acetamide

IR (neat) cm$^{-1}$: 2927, 1672; NMR (CDCl$_3$) δ: 0.4–2.0 (27H, m), 2.09 (3H, s), 3.37 (3H, s) 7.23 (1H, d, J=8.3 Hz), 7.80 (1H, dd, J=8.3, 1.5 Hz), 8.4–8.6 (1H, brs).

N,N-Dimethyl-N-[5-(1,1,1-tributylstannyl)-2-pyridyl]amine

IR (neat) cm$^{-1}$: 2926; NMR (CDCl$_3$) δ: 0.6–2.0 (27H, m), 3.07 (6H,s), 6.53 (1H, d, J=8.3 Hz) 7.49 (1H, dd, J=8.3, 1.7 Hz), 8.1–8.2 (1H, brs).

2,3-Dimethyl-5-(1,1,1-tributylstannyl)pyridine

IR (neat) cm$^{-1}$: 2957, 2926; NMR (CDCl$_3$) δ: 0.6–1.8 (27H, m), 2.31 (3H, s), 2.60 (3H, s), 7.6–7.7 (1H, brs), 8.2–8.3 (1H, brs).

Benzyl N-methyl-N-{[3-methyl-5-(1,1,1-tributylstannyl)-2-pyridyl]methyl}carbamate NMR (CDCl$_3$) δ: 0.8–2.0 (27H, m), 2.1–2.4 (3H, m), 2.95 (3H, s), 4.62 (2H, s), 5.18 (2H, s), 7.2–7.6 (6H, m), 8.39 (1H, s).

N'1-Acetyl-N'1-methyl-N1-[5-(1,1,1-tributylstannyl)-2-pyridyl]ethanchydrazide

NMR (CDCl$_3$) δ: 0.8–1.8 (27H, m), 2.42 (6H, s), 3.35 (3H, s), 6.51 (1H, d, J=8.3 Hz), 7.58 (1H, dd, J=8.3, 1.6 Hz), 8.20 (1H, d, J=1.6 Hz).

2-Methyl-5-(1,1,1-tributylstannyl)pyridine

IR (neat) cm$^{-1}$: 2956, 2925; NMR (CDCl$_3$) δ: 0.8–1.8 (27H, m), 2.53 (3H, s), 7.11 (1H, d, j=7.6 Hz), 7.64 (1H, d, J=7.6 Hz), 8.91 (1H, s).

3-Methyl-5-(1,1,1-tributylstannyl)pyridine

NMR (CDCl$_3$) δ: 0.8–1.6 (27H, m), 2.30 (3H, s), 7.5–7.6 (1H, brs), 8.2–8.5 (2H, m).

3-(Acetoxymethyl)-5-(1,1,1-tributylstannyl)pyridine

NMR (CDCl$_3$) δ: 0.8–1.8 (27H, m), 2.11 (3H, s), 5.09 (2H, s), 7.7–7.8 (1H, m), 8.4–8.6 (2H, m).

3-{[(benzyloxy)carbonyl]amino}-5-(1,1,1-tributylstannyl)pyridine

NMR (CDCl$_3$) δ: 0.8–1.6 (27H, m), 5.22 (2H, s), 6.6–6.8 (1H, brs), 7.39 (5H, s), 7.9–8.0 (1H, m), 8.2–8.3 (1H, m), 8.4–8.5 (1H, m).

2,3-Di(acetylamino)-5-(1,1,1-tributylstannyl)pyridine

NMR (CDCl$_3$) δ: 0.8–1.8 (27H, m), 2.16 (3H, s), 2.28 (3H, s), 8.0–8.1 (1H, m), 8.3–8.4 (1H, m), 8.7–9.0 (1H, brs), 9.2–9.4 (1H, brs).

N1-[5-(1,1,1-tributylstannyl)-2-pyridyl]acetamide

IR (neat) cm$^{-1}$: 2956, 2926, 1702, 1686; NMR (CDCl$_3$) δ: 0.6–2.0 (27H, m), 2.19 (3H, s), 7.76 (1H, d, J=8.1 Hz), 8.1–8.4 (2H, m), 9.3–9.5 (1H, brs).

1-Cyclopropyl-8-methyl-4-oxo-7-(1,1,1-tributylstannyl)-1,4-dihydro-3-quinolinecarboxylic acid ethyl ester IR (neat) cm$^{-1}$: 2955, 2923, 1725, 1602; NMR (CDCl$_3$) δ: 0.6–2.0 (34H, m), 2.83 (3H, s), 3.8–4.2 (1H, m), 4.39 (2H, q, J=6.8 Hz), 7.42 (1H, d, J=7.8 Hz), 8.22 (1H, d, J=7.8 Hz), 8.68 (1H, s).

Reference Example 16

Under a nitrogen atmosphere, 20.0 g of 3-bromo-2-methylaniline was dissolved in 140 ml of methanol. After adding 20.6 g of 1-ethoxy-1-trimethylsilyloxycyclopropane and 25.8 g of acetic acid to the solution, the resulting mixture was refluxed at 65° C. for 4 hours. Evaporation of the solvent under reduced pressure afforded 27.5 g of yellow oil of N-(1-methoxy)cyclopropyl-3-bromo-2-methylaniline.

Reference Example 17

Under a nitrogen atmosphere, 5.29 g of sodium borohydride was suspended in 160 ml of anhydrous tetrahydrofuran and under ice cooling, 19.8 g of a boron trifluoride ether complex was dropped to the suspension over 10 minutes. The mixture was stirred at the same temperature as above for 1.5 hours. At the same temperature as above, 80 ml of a tetrahydrofuran solution containing 27.5 g of N-(1-methoxy)cyclopropyl-3-bromo-2-methylaniline was added and the mixture was stirred at 50 to 55° C. for 3 hours. The reaction mixture was added to ice water and after stirring for 30 minutes under ice cooling, the reaction mixture was extracted with ethyl acetate to separate an organic layer. The obtained organic layer was washed with water and with saturated saline in order and dried over anhydrous magnesium sulfate and the solvent was evaporated under reduced pressure. Evaporation of the obtained residue under reduced pressure afforded 20.3 g of colorless oil of N-cyclopropyl-3-bromo-2-methylaniline. Boiling point: 140 to 150° C. (10 mmHg)

Reference Example 18

To a solution of 3.00 g of 3-chloro-2-methylaniline in a mixed solvent consisting of 6 ml of water and 30 ml of dioxane were added 6.36 g of 6-[(2,2-dimethylpropanoyl)(methyl)-amino]-5-methyl-3-pyridyl borate, 13.5 g of tripotassium phosphate and 0.31 g of bis(tricyclohexylphosphine)palladium (II) chloride and the mixture was refluxed for 8 hours under a nitrogen atmosphere. The reaction mixture was added to a mixed solvent consisting of 15 ml of water and 15 ml of ethyl acetate and an organic layer was separated. The obtained organic layer was washed with water and with saturated saline in order and dried over anhydrous magnesium sulfate and the solvent was evaporate d under reduce d pressure. Addition of ethyl acetate to the obtained residue and filtration of the crystals afforded 4.95 g of colorless crystals of N-[5-(3-amino-2-methylphenyl) -3-methyl-2-pyridyl]-N,2,2-trimethylpropanamide.

IR (KBr) cm$^{-1}$: 3449, 3355, 1625; NMR (CDCl$_3$) δ: 1.09 (9H, s), 2.06 (3H, s), 2.32 (3H, s), 3.23 (3H, s), 3.8 (2H, brs), 6.6–6.9 (2H, m), 7.0–7.2 (1H, m), 7.54 (1H, d, J=2.2 Hz), 8.28 (1H, d, J=2.2 Hz).

Reference Example 19

To a suspension of 5.70 g of N-[5-(3-amino-2-methylphenyl)-3-methyl-2-pyridyl]-N,2,2-trimethylpropanamide in 34.2 ml of methanol were added 4.40 g of acetic acid and 4.32 g of 1-ethoxy-1-trimethylsilyloxycyclopropane and the mixture was refluxed for 7 hours under a nitrogen atmosphere. Concentration of the reaction mixture under reduced pressure afforded 6.98 g of N-(5-{3-[(1-methoxycyclopropyl)amino]-2-methylphenyl}-3-methyl-2-pyridyl)-N,2,2-trimethylpropanamide.

Reference Example 20

To a suspension of 6.98 g of N-(5-[3-(1-methoxycyclopropyl) amino]-2-methylphenyl)-3-methyl-2-pyridyl-N,2,2-trimethylpropanamide in 70 ml of isopropanol was added 3.46 g of sodium borohydride and the mixture was refluxed for 33 hours. After cooling the reaction mixture to room temperature, 26.9 ml of acetone was dripped thereto over 30 minutes. After stirring at the same temperature for 1 hour, the reaction mixture was added to a mixed solvent consisting of 70 ml of water and 70 ml of ethyl acetate and an organic layer was separated. The obtained organic layer was washed with water and with saturated saline in order and dried over anhydrous magnesium sulfate and the solvent was evaporated under reduced pressure. Purification of the obtained residue by silica gel column chromatography [eluent; hexane:ethyl acetate=5:1] afforded 3.19 g of colorless crystals of N-{5-[3-(cyclopropylamino)-2-methylphenyl]-3-methyl-2-pyridyl}-N,2,2-trimethylpropanamide.

IR (KBr) cm$^{-1}$: 3370, 1638; NMR (CDCl$_3$) δ: 0.5–1.3 (13H, m), 1.98 (3H, s), 2.2–2.7 (4H, m), 3.23 (3H, s), 4.1–4.3 (1H, brs), 6.67 (1H, dd, J=6.3 Hz, 2.4 Hz), 7.0–7.4 (2H, m), 7.52 (1H, d, J=1.8 Hz), 8.27 (1H, d, J=1.8 Hz).

Reference Example 21

To a solution of 0.20 g of 3-chloro-2-methylaniline in 4 ml of 1,2-dimethoxyethane were added 0.49 g of N-[5-(1,3,2-dioxaborinan-2-yl)-3-methyl-2-pyridyl]-N-2,2-trimethylpropanamide, 0.90 g of tripotassium phosphate and 0.046 g of bis(triphenylphosphine)nickel (II) chloride, and the mixture was refluxed for 6 hours under a nitrogen atmosphere. The reaction mixture was added to a mixed solvent consisting of 10 ml of water and 10 ml of methylene chloride and an organic layer was separated. The separated organic layer was dried over anhydrous magnesium sulfate and then the solvent was evaporated. Purification of the obtained residue by silica gel column chromatography [eluent; hexane:ethyl acetate=2:1] afforded 0.23 g of colorless crystals of N-[5-(3-amino-2-methylphenyl)-3-methyl-2-pyridyl]-N,2,2-trimethyl-propanamide. The physical data coincided with those of the compound obtained in Reference Example 18.

Reference Example 22

A mixture of 80 g of N-(5-bromo-3-methyl-2-pyridyl)-N-methylamine, 76.8 g of pivaloyl chloride and 50.4 g of pyridine was dissolved in 400 ml of toluene and the resulting solution was stirred at 100 ° C. for 10.5 hours. The reaction mixture was added to 800 ml of ice water and adjusted to pH 12 with an aqueous 5 mol/l sodium hydroxide solution and an organic layer was separated. To the obtained organic layer was added 560 ml of water and the mixture was adjusted to pH 1 with 1 mol/l hydrochloric acid. Thereafter, an organic layer was separated. The obtained organic layer was washed with water and with saturated saline in order and dried over anhydrous magnesium sulfate and the solvent was evaporated under reduced pressure. Purification of the obtained residue by distillation under reduced pressure afforded 91.6 g of pale yellow oil of N-(5-bromo-3-methyl-2-pyridyl)-N,2,2-trimethylpropanamide.

IR (neat) cm$^{-1}$: 2958, 1648; NMR (CDCl$_3$) δ: 1.06 (9H, s), 2.28 (3H, s), 3.15 (3H, s), 7.75 (1H, d, J=2.3 Hz), 8.39 (1H, d, J=2.3 Hz); Boiling point: 145–165° C. (10 mmHg).

Reference Example 23

To a solution of 70 g of N-(5-bromo-3-methyl-2-pyridyl)-N,2,2-trimethylpropanamide in 1,050 ml of diethyl ether was dropped 177 ml of an-hexane solution (1.53 M solution) of n-butyllithium at −70 ° C. over 30 minutes. After stirring at the same temperature for 30 minutes, the temperature was elevated to −15° C. and 59 g of acetic acid was added. The temperature was elevated to room temperature and the mixture was stirred at the same temperature for 1 hour. The reaction mixture was added to 1,050 ml of water and adjusted to pH 11.5 with an aqueous 5 ml/l sodium hydroxide solution and an aqueous layer was separated. To the obtained aqueous layer was added 770 ml of ethyl acetate and after adjusting the mixture to pH 4 with 6 mol/l hydrochloric acid, an organic layer was separated. The obtained organic layer was washed with water and with saturated saline in order and dried over anhydrous magnesium sulfate. Evaporation of the solvent under reduced pressure afforded 41.5 g of pale yellow solids of 6-[(2,2-dimethylpropanoyl)(methyl)amino]-5-methyl-3-pyridyl borate.

IR (KBr) cm$^{-1}$: 3412, 2965, 1618; NMR (CDCl$_3$) δ: 1.06 (9H, s), 2.29 (3H, s), 3.19 (3H, s), 8.0–8.2 (1H, m), 8.6–9.0 (1H, m).

Reference Example 24

To a solution of 9.99 g of 6-[(2,2-dimethylpropanoyl)(methyl)amino]-5-methyl-3-pyridyl borate in 50 ml of ethyl acetate were added 3.00 g of anhydrous magnesium sulfate and 3.00 g of trimethylene glycol and the mixture was stirred at room temperature for 3 hours. After filtering the insoluble matter, the solvent was evaporated under reduced pressure. Purification of the obtained residue by silica gel column chromatography [chloroform:ethanol=30:1] afforded 8.33 g of colorless crystals of N-[5-(1,3,2-dioxaborinan-2-yl)-3-methyl-2-pyridyl]-N,2,2-trimethylpropanamide.

IR (KBr) cm$^{-1}$: 1638, 1323; NMR (CDCl$_3$) δ: 1.01 (9H, s), 1.9–2.5 (5H, m), 3.14 (3H, s), 4.19 (4H, t, J=5.5 Hz), 7.9–8.2 (1H, m), 8.63 (1H, d, J=1.5 Hz).

EXAMPLE 1

To a suspension of 2.00 g of 7-bromo-1-cyclopropyl-8-methyl-4-oxo-1,4-dihydro-3-quinolinecarboxylic acid ethyl ester in 20 ml of toluene were added 2.3 g of 2,6-dimethyl-4-(tributylstannyl)pyridine and 0.08 g of bis (triphenylphosphine)palladium (II) chloride and the mixture was refluxed for 3 hours under a nitrogen atmosphere. Concentration of the reaction mixture under reduced pressure, purification of the obtained residue by column chromatography [eluent; chloroform:ethanol=50:1] and addition of diethyl ether followed by filtration of precipitates afforded 1.77 g of colorless crystals of 1-cyclopropyl-7-(2,6-dimethyl-4-pyridyl)-8-methyl-4-oxo-1,4-dihydro-3-quinolinecarboxylic acid ethyl ester.

IR (KBr) cm$^{-1}$: 1730; NMR (CDCl$_3$) δ: 0.8–1.6 (7H, m), 2.61 (9H, s), 3.80–4.20 (1H, m), 4.41 (2H, q, J=7.1 Hz), 6.96 (2H, s), 7.23 (1H, d, J=7.6 Hz), 8.36 (1H, d, j=7.6 Hz), 8.74 (1H, s).

Similarly, the following compounds were obtained.

1-Cyclopropyl-7-(5,6-dimethyl-3-pyridyl)-8-methyl-4-oxo-1,4-dihydro-3-quinolinecarboxylic acid ethyl ester IR (KBr) cm$^{-1}$: 1722; NMR (CDCl$_3$) δ: 0.8–1.6 (7H, m), 2.41 (3H, s), 2.63 (3H, s), 2.65 (3H, s), 3.8–4.2 (1H, m), 4.41 (2H, q, J=7.1 Hz), 7.27 (1H, d, J=8.1 Hz), 7.5–7.6 (1H, brs), 8.3–8.5 (2H, m), 8.74 (1H, s).

1-Cyclopropyl-7-(6-methoxy-3-pyridyl)-8-methyl-4-oxo-1,4-dihydro-3-quinolinecarboxylic acid ethyl ester IR (KBr) cm$^{-1}$: 1726; NMR (CDCl$_3$) δ: 0.8–1.6 (7H, m), 2.64 (3H, s), 3.8–4.2 (4H, m), 4.40 (2H, q, J=7.1 Hz), 6.86 (1H, d, J=8.6 Hz), 7.28 (1H, d, J=8.2 Hz), 7.63 (1H, dd, J=8.6, 2.4 Hz), 8.20(1H, d, J=2.4 Hz), 8.34 (1H, d, J=8.2 Hz), 8.73 (1H, s).

7-[6-(Acetylamino)-5-methyl-3-pyridyl]-1-cyclopropyl-8-methyl-4-oxo-1,4-dihydro-3-quinolinecarboxylic acid ethyl ester IR (KBr) cm$^{-1}$: 3258, 1728, 1695; NMR (CDCl$_3$) δ: 0.8–1.6(7H, m), 2.33 (3H, s), 2.38 (3H, s), 2.64 (3H, s), 3.9–4.2 (1H, m), 4.39 (2H, q, J=7.1 Hz), 7.26 (1H, d, J=8.2 Hz), 7.59 (1H, d, J=2.1 Hz), 8.27 (1H, d, J=2.1 Hz), 8.35 (1H, d, J=8.2 Hz), 8.4–8.6 (1H, brs), 8.74 (1H, s).

7-{6-[Acetyl(methyl)amino]-5-methyl-3-pyridyl}-1-cyclopropyl-8-methyl-4-oxo-1,4-dihydro-3-quinolinecarboxylic acid ethyl ester IR (KBr) cm$^{-1}$: 1725, 1663; NMR (CDCl$_3$) δ: 0.8–1.6 (7H, m), 1.88 (3H, s), 2.38(3H, s), 2.66 (3H, s), 3.28 (3H, s), 3.9–4.1 (1H, m), 4.41 (2H, q, J=7.1 Hz), 7.30 (1H, d, J=8.3 Hz), 7.69 (1H, d, J=1.7 Hz), 8.3–8.5 (2H, m), 8.75 (1H, s).

1-Cyclopropyl-7-[6-(dimethylamino)-5-methyl-3-pyridyl]-8-methyl-4-oxo-1,4-dihydro-3-quinolinecarboxylic acid ethyl ester IR (KBr) cm$^{-1}$: 1718; NMR (CDCl$_3$) δ: 0.8–1.6 (7H, m), 2.38 (3H,s), 2.65 (3H, s), 2.96 (6H, s), 3.9–4.1 (1H, m), 4.40 (2H, q, J=7.1 Hz), 7.29 (1H, d, J=8.2 Hz), 7.40 (1H, d, J=2.2 Hz), 8.15 (1H, d, J=2.2 Hz), 8.33 (1H, d, J=8.2 Hz), 8.73 (1H, s).

7-{6-[Acetyl(methyl)amino]-3-pyridiyl}-1-cyclopropyl-8-methyl-4-oxo-1,4-dihydro-3-quinolinecarboxylic acid ethyl ester IR (KBr) cm$^{-1}$: 1724, 1661; NMR (CDCl$_3$) δ: 0.8–1.6 (7H, m), 2.25 (3H, s), 2.67 (3H, s), 3.50 (3H, s), 3.9–4.1 (1H, m), 4.41 (2H, q, J=7.1 Hz), 7.30 (1H, d, J=8.2 Hz), 7.55 (1H, d, J=8.2 Hz), 7.79 (1H, dd, J=8.2, 2.3 Hz), 8.38 (1H, d, J=8.2 Hz), 8.50 (1H, d, J=2.3 Hz), 8.74 (1H, s).

1-Cyclopropyl-7-[6-(dimethylamino)-3-pyridyl]-8-methyl-4-oxo-1,4-dihydro-3-quinolinecarboxylic acid ethyl ester IR (KBr) cm$^{-1}$: 1721; NMR (CDCl$_3$) δ: 0.8–1.6 (7H, m), 2.66 (3H, s), 3.17 (6H, s), 3.8–4.2 (1H, m), 4.40 (2H, q, J=7.1 Hz), 6.62 (1H, d, J=8.7 Hz), 7.29 (1H, d, J=8.2 Hz), 7.52 (1H, dd, J=8.7, 2.3 Hz), 8.23 (1H, d, J=2.3 Hz), 8.32 (1H, d, J=8.2 Hz), 8.72 (1H, s).

1-Cyclopropyl-8-methyl-4-oxo-7-(4-pyridyl)-1,4-dihydro-3-quinolinecarboxylic acid ethyl ester IR (KBr) cm$^{-1}$: 1725; NMR (CDCl$_3$) δ: 0.8–1.6 (7H, m), 2.63 (3H, s), 3.9–4.2 (1H, m), 4.40 (2H, q, J=7.1 Hz), 7.2–7.4 (3H, m), 8.37 (1H, d, J=8.3 Hz), 8.6–8.9 (3H, m).

1-Cyclopropyl-7-(2,6-dimethyl-4-pyridyl)-5,8-dimethyl-4-oxo-1,4-dihydro-3-quinolinecarboxylic acid ethyl ester IR (KBr) cm$^{-1}$: 1729; NMR (CDCl$_3$) δ: 0.8–1.6 (7H, m), 2.49 (3H, s), 2.61 (6H, s), 2.89 (3H, s), 3.9–4.1 (1H, m), 4.40 (2H, q, J=7.1 Hz), 6.9–7.1 (3H, brs), 8.63 (1H, s).

7-[6-({[(Benzyloxy)carbonyl](methyl)amino}methyl)-5-methyl-3-pyridyl]-1-cyclopropyl-8-methyl-4-oxo-1,4-dihydro-3-quinolinecarboxylic acid ethyl ester IR (KBr) cm$^{-1}$: 1717, 1700; NMR (CDCl$_3$) δ: 0.8–1.6 (7H, m), 2.40 (3H, s), 2.61 (3H, s), 3.04 (3H, s), 3.8–4.2 (1H, m), 4.41 (2H, q, J=7.1 Hz), 4.70 (2H, s), 5.19 (2H, s), 7.2–7.6 (7H, m), 8.3–8.5 (2H, m), 8.74 (1H, s).

1-Cyclopropyl-8-methyl-4-oxo-7-(3-pyridyl)-1,4-dihydro-3-quinolinecarboxylic acid ethyl ester IR (KBr) cm$^{-1}$: 1733; NMR (CDCl$_3$) δ: 0.8–1.6 (7H, m), 2.63 (3H, s), 3.9–4.2 (1H, m), 4.42 (2H, q, J=7.1 Hz), 7.2–7.8 (3H, m), 8.40 (1H, d, J=8.3 Hz), 8.6–8.9 (3H, m).

1-Cyclopropyl-7-[6-(1,2-diacetyl-2-methylhydrazino)-3-pyridyl]-8-methyl-4-oxo-1,4-dihydro-3-quinolinecarboxylic acid ethyl ester IR (KBr) cm$^{-1}$: 1734, 1686; NMR (CDCl$_3$) δ: 0.8–1.6 (7H, m), 2.47 (6H, s), 2.64 (3H, s), 3.43 (3H, s), 3.7–4.2 (1H, m), 4.40 (2H, q, J=7.2 Hz), 6.63 (1H, d, J=8.1 Hz), 7.0–7.7 (2H, m), 8.1–8.4 (2H, m), 8.72 (1H, s).

5-{[(Benzyloxy)carbonyl]amino}-1-cyclopropyl-7-(2,6-dimethyl-4-pyridyl)-8-methyl-4-oxo-1,4-dihydro-3-quinclinecarboxylic acid ethyl ester IR (KBr) cm$^{-1}$: 1718; NMR (CDCl$_3$) δ: 0.8–1.5 (7H, m), 2.45 (3H, s), 2.60 (6H, s), 3.9–4.1 (1H, m), 4.40 (2H, q, J=7.1 Hz), 5.18 (2H, s), 6.98 (2H, s), 7.3–7.5 (6H, m), 8.32 (1H, s), 8.66 (1H, s).

5-{[(Benzyloxy)carbonyl]amino}-1-cyclopropyl-7-(5,6-dimethyl-3-pyridyl)-8-methyl-4-oxo-1,4-dihydro-3-quinolinecarboxylic acid ethyl ester IR (KBr) cm$^{-1}$: 1727; NMR (CDCl$_3$) δ: 0.8–1.6 (7H, m), 2.36 (3H, s), 2.47 (3H, s), 2.57 (3H, m), 3.9–4.1 (1H, m), 4.40 (2H, q, J=7.1 Hz), 5.18 (2H, s), 7.2–7.6 (7H, m), 8.2–8.5 (2H, brs), 8.66 (1H, s).

1-Cyclopropyl-7-(6-methyl-3-pyridyl)-8-methyl-4-oxo-1,4-dihydro-3-quinolinecarboxylic acid ethyl ester IR (KBr) cm$^{-1}$: 1718; NMR (CDCl$_3$) δ: 0.9–1.5 (7H, m), 2.63 (3H, s), 2.65 (3H, s), 3.9–4.1 (1H, m), 4.41 (2H, q, J=7.1 Hz), 7.2–7.4 (2H, m), 7.62 (1H, dd, J=8.1, 2.2 Hz), 8.37 (1H, d, J=8.1 Hz), 8.54 (1H, d, J=2.2 Hz), 8.74 (1H, s).

1-Cyclopropyl-7-(5-methyl-3-pyridyl)-8-methyl-4-oxo-1,4-dihydro-3-quinolinecarboxylic acid ethyl ester IR (KBr) cm$^{-1}$: 1684; NMR (CDCl$_3$) δ: 0.9–1.5 (7H, m), 2.44 (3H, s), 2.62 (3H, s), 3.9–4.1 (1H, m), 4.41 (2H, q, J=7.1 Hz), 7.2–7.4 (1H, m), 7.5–7.6 (1H, m), 8.3–8.6 (3H, m), 8.74 (1H, s).

7-[5-(Acetoxymethyl)-3-pyridyl]-1-cyclopropyl-8-methyl-4-oxo-1,4-dihydro-3-quinolinecarboxylic acid ethyl ester NMR (CDCl$_3$) δ: 0.9–1.5 (7H, m), 2.14 (3H, s), 2.63 (3H, s), 3.9–4.1 (1H, m), 4.41 (2H, q, J=7.1 Hz), 5.22 (2H, s), 7.2–7.4 (1H, m), 7.7–7.8 (1H, brs), 8.38 (1H, d, J=8.3 Hz), 8.6–8.8 (3H, m).

7-(5-{[(Benzyloxy)carbonyl]amino}-3-pyridyl)-1-cyclopropyl-8-methyl-4-oxo-1,4-dihydro-3-quinoline-carboxylic acid ethyl ester NMR (CDCl$_3$) δ: 0.9–1.5 (7H, m), 2.62 (3H, s), 3.9–4.1 (1H, m), 4.38 (2H, q, J=7.1 Hz), 5.22 (2H, s), 7.2–7.7 (7H, m), 8.0–8.2 (1H, brs), 8.3–8.4 (2H, m), 8.5–8.7 (1H, m), 8.73 (1H, s).

1-Cyclopropyl-7-[5,6-di(acetylamino)-3-pyridyl]-8-methyl-4-oxo-1,4-dihydro-3-quinolinecarboxylic acid ethyl ester IR (KBr) cm$^{-1}$: 3262, 1720, 1691; NMR (CDCl$_3$) δ: 0.9–1.5 (7H, m), 2.20 (3H, s), 2.36 (3H, s), 2.67 (3H, s), 3.9–4.1 (1H, m), 4.40 (2H, q, J=7.1 Hz), 7.31 (1H, d, J=7.8 Hz), 8.14 (1H, d, J=2.0 Hz), 8.3–8.5 (2H, m), 8.6–8.8 (2H, brs), 9.5–9.7 (1H, brs).

7-[6-(Acetylamino)-3-pyridyl]-1-cyclopropyl-8-methyl-4-oxo-1,4-dihydro-3-quinolinecarboxylic acid ethyl ester IR (KBr) cm$^{-1}$: 3262, 1734, 1702; NMR (CDCl$_3$) δ: 0.8–1.6 (7H, m), 2.27 (3H, s), 2.63 (3H, s), 3.8–4.2 (1H, m), 4.41 (2H, q, J=7.2 Hz), 7.2–7.4 (1H, m), 7.74 (1H, dd, J=8.8, 2.2 Hz), 8.1–8.5 (4H, m), 8.74 (1H, s).

7-[6-(Acetylamino-5-methyl-3-pyridyl]-1-cyclopropyl-8-(difluoromethoxy)-4-oxo-1,4-dihydro-3-quinolinecarboxylic acid ethyl ester IR (KBr) cm$^{-1}$: 1732, 1683; NMR (CDCl$_3$) δ: 0.8–1.6 (7H, m), 2.36 (3H, s), 2.38 (3H, s), 3.95–4.30 (1H, m), 4.41 (2H, q, J=7.1 Hz), 5.98 (1H, t, J=74.3 Hz), 7.42 (1H, d, J=8.3 Hz), 7.78 (1H, m), 7.89 (1H, brs), 8.3–8.6 (2H, m), 8.68 (1H, s).

1-Cyclopropyl-7-(2,6-dimethyl-4-pyridyl)-8-(difluoromethoxy)-4-oxo-1,4-dihydro-3-quinolinecarboxylic acid ethyl ester IR (KBr) cm$^{-1}$: 1721, 1626, 1602; NMR (CDCl$_3$) δ: 0.9–1.5 (7H, m), 2.63 (6H, s), 4.0–4.2 (1H, m), 4.41 (2h, q, J=7.1 Hz), 5.92 (1H, t, J=75 Hz), 7.18 (2H, s), 7.42 (1H, d, J=8.3 Hz), 8.47 (1H, d, J=8.3 Hz), 8.69 (1H, s).

7-[6-(Acetylamino)-5-methyl-3-pyridyl]-1-cyclopropyl-8-methoxy-4-oxo-1,4-dihydro-3-quinolinecarboxylic acid ethyl ester IR (KBr) cm$^{-1}$: 3255, 1728, 1697; NMR (CDCl$_3$) δ: 0.9–1.7 (7H, m), 2.35 (3H, s), 2.38 (3H, s), 3.41 (3H, s), 3.8–4.2 (1H, m), 4.40 (2H, q, J=7.1 Hz), 7.37 (1H, d, J=8.3 Hz), 7.7–8.0 (2H, m), 8.32 (1H, d, J=8.3 Hz), 8.53 (1H, d, J=2.2 Hz), 8.67 (1H, s).

EXAMPLE 2

To a solution of 2.07 g of 5-bromo-2,3,4-trimethyl-pyridine in 45 ml of N,N-dimethylformamide were added 2.40 g of silver (I) oxide and 0.66 g of tetrakis(triphenylphosphine)palladium (0) and the mixture was refluxed for 10 minutes under an argon atmosphere. Then, a solution of 1.29 g of 1-cyclopropyl-8-methyl-4-oxo-7-(1,1,1-tributyl-stannyl)-1,4-dihydro-3-quinolinecarboxylic acid ethyl ester in 5 ml of N,N-dimethylformamide was added thereto and the mixture was refluxed for 30 minutes. The reaction mixture was concentrated under reduced pressure. Purification of the obtained residue by column chromatography [eluent; ethyl acetate] afforded 0.62 g of 1-cyclopropyl-8-methyl-4-oxo-7-(4,5,6-trimethyl-3-pyridyl)-1,4-dihydro-3-quinolinecarboxylic acid ethyl ester.

IR (KBr) cm$^{-1}$: 1728; NMR (CDCl$_3$) δ: 0.8–1.6 (7H, m), 2.11 (3H, s), 2.35 (3H, s), 2.46 (3H, s), 2.72 (3H, s), 3.8–4.1 (1H, m), 4.41 (2H, q, J=7.1 Hz), 7.14 (1H, d, J=8.1 Hz), 8.18 (1H, s), 8.38 (1H, d, J=8.1 Hz), 8.73 (1H, s).

Similarly, the following compound was obtained.
1-Cyclopropyl-7-(4,6-dimethyl-3-pyridyl)-8-ethyl-4-oxo-1,4-dihydro-3-quinolinecarboxylic acid ethyl ester IR (KBr) cm$^{-1}$: 1719; NMR, (CDCl$_3$) δ: 0.8–1.6 (7H, m), 2.15 (3H, s), 2.48 (3H, s), 2.69 (3H, s), 3.8–4.2 (1H, m), 4.41 (2H, q, J=7.1 Hz), 7.16 (1H, d, J=8.2 Hz), 7.24 (1H, s), 8.30(1H, s), 8.38 (1H, d, J=8.2 Hz), 8.74 (1H, s).

EXAMPLE 3

To a suspension of 1.77 g of 1-cyclopropyl-7-(2,6-dimethyl-4-pyridyl) -8-methyl-4-oxo-1,4-dihydro-3-quinolinecarboxylic acid ethyl ester in 18 ml of ethanol was added 18ml of an aqueous 1 mol/l sodium hydroxide solution and the mixture was stirred at room temperature for 1 hour. Addition of 18 ml of 1 mol/l hydrochloric acid and filtration of precipitates afforded 1.52 g of colorless crystals of 1-cyclopropyl-7-(2,6-dimethyl-4-pyridyl)-8-methyl-4-oxo-1,4-dihydro-3-quinolinecarboxylic acid.

IR (KBr) cm$^{-1}$: 1718, 1607; NMR (CDCl$_3$) δ: 1.00–1.60 (4H, m), 2.63 (6H, s), 2.70 (3H, s), 4.00–4.40 (1H, m), 6.98 (2H, s), 7.38 (1H, d, J=8.1 Hz), 8.38 (1H, d, J=8.1 Hz), 9.00 (1H, s).

Similarly, the following compounds were obtained.
1-Cyclopropyl-8-methyl-4-oxo-7-(4,5,6-trimethyl-3-pyridyl)-1,4-dihydro-3-quinolinecarboxylic acid IR (KBr) cm$^{-1}$: 1727, 1610; NMR (CDCl$_3$) δ: 0.8–1.5 (4H, m), 2.10 (3H, s), 2.35 (3H, s), 2.56 (3H, s), 2.68 (3H, s), 3.9–4.4 (1H, m), 7.31 (1H, d, J=8.1 Hz), 8.16 (1H, s), 8.41 (1H, d, J=8.1 Hz), 9.01 (1H, s), 14.6–14.8 (1H, brs).
1-Cyclopropyl-7-(5,6-dimethyl-3-pyridyl)-8-methyl-4-oxo-1,4-dihydro-3-quinolinecarboxylic acid IR (KBr) cm$^{-1}$: 1716, 1616; NMR (CDCl$_3$) δ: 0.8–1.6 (4H, m), 2.42 (3H, s), 2.64 (3H, s), 2.71 (3H, s) 3.9–4.4 (1H, m), 7.3–7.7 (1H, m), 8.2–8.6 (2H, m), 9.01 (1H, s), 14.6–14.8 (1H, brs).
1-Cycloprpyl-7-(6-methoxy-3-pyridyl)-8-methyl-4-oxo-1,4-dihydro-3-quinolinecarboxylic acid IR (KBr) cm$^{-1}$: 1719; NMR (CDCl$_3$) δ: 1.0–1.4 (4H, m), 2.71 (3H, s), 3.9–4.3 (4H, m), 6.89 (1H, d, J=8.6 Hz), 7.43 (1H, d, J=8.2 Hz), 7.63 (1H, dd, J=8.6, 2.4 Hz), 8.22 (1H, d, J=2.4 Hz), 8.39 (1H, d, J=8.2 Hz), 9.00 (1H, s), 14.70 (1H, brs). Melting point: equal to or higher than 250° C.
7-{6-[Acetyl(methylamino]-5-methyl-3-pyridyl}-1-cyclopropyl-8-methyl-4-oxo-1,4-dihydro-3-quinolinecarboxylic acid IR (KBr) cm$^{-1}$: 1735, 1673; NMR (CDCl$_3$) δ: 1.0–1.5 (4H, m), 1.89 (3H, s), 2.40 (3H, s), 2.75 (3H, s), 3.29 (3H, s), 4.0–4.3 (1H, m), 7.46 (1H, d, J=8.2 Hz), 7.6–7.8 (1H, brs), 8.3–8.5 (2H, m), 9.01 (1H, s), 14.60 (1H, brs). Melting point: equal to or higher than 250° C.

1-Cyclopropyl-7-[6-(dimethylamino)-5-methyl-3-pyridyl]-8-methyl-4-oxo-1,4-dihydro-3-quinolinecarboxylic acid IR (KBr) cm$^{-1}$: 1733; NMR (CDCl$_3$) δ: 0.9–1.5 (4H, m), 2.40 (3H, s), 2.74 (3H, s), 2.98 (6H, s), 4.0–4.3 (1H, m), 7.3–7.5 (2H, m), 8.16 (1H, d, J=2.2 Hz), 8.35 (1H, d, J=8.3 Hz), 8.99 (1H, s), 14.80 (1H, brs). Melting point: equal to or higher than 250° C.
7-{6-[Acetyl(methyl)amino]-3-pyridyl}-1-cyclopropyl-8-methyl-4-oxo-1,4-dihydro-3-quinolinecarboxylic acid IR (KBr) cm$^{-1}$: 1725, 1673; NMR (CDCl$_3$) δ: 0.9–1.4 (4H, m), 2.28 (3H, s), 2.74 (3H, s), 3.52 (3H, s), 4.0–4.4 (1H, m), 7.46 (1H, d, J=8.3 Hz), 7.62 (1H, d, J=8.3 Hz), 7.80 (1H, dd, J=8.3, 2.4 Hz), 8.42 (1H, d, J=8.3 Hz), 8.51 (1H, d, J=2.4 Hz), 9.02 (1H, s).
1-Cyclopropyl-7-[6-(dimethylamino)-3-pyridyl]-8-methyl-4-oxo-1,4-dihydro-3-quinolinecarboxylic acid IR (KBr) cm$^{-1}$: 1705; NMR (CDCl$_3$) δ: 0.9–1.5 (4H, m), 2.74 (3H, s), 3.18 (6H, s), 4.0–4.3 (1H, m), 6.64 (1H, d, J=8.8 Hz), 7.4–7.6 (2H, m), 8.2–8.4 (2H, m), 8.98 (1H, s), 14.80(1H, brs). Melting point: equal to or higher than 250° C.
1-Cyclopropyl-8-methyl-4-oxo-7-(4-pyridyl)-1,4-dihydro-3-quinolinecarboxylic acid IR (KBr) cm$^{-1}$: 1717; NMR (CDCl$_3$) δ: 1.0–1.4 (4H, m), 2.68 (3H, s), 4.2–4.6 (1H, m), 7.4–7.7 (3H, m), 8.28 (1H, d, J=8.3 Hz), 8.7–8.9 (2H, m), 8.92 (1H, s), 14.75 (1H, brs). Melting point: equal to or higher than 250° C.
1-Cyclopropyl-7-(2,6-dimethyl-4-pyridyl)-5,8-dimethyl-4-oxo-1,4-dihydro-3-quinolinecarboxylic acid IR (KBr) cm$^{-1}$: 1719; NMR (CDCl$_3$) δ: 0.8–1.4 (4H, m), 2.58 (3H, s), 2.62 (6H, s), 2.90 (3H, s), 4.0–4.3 (1H, m), 6.9–7.1 (2H, brs), 7.11 (1H, s), 8.94 (1H, s), 15.05 (1H, brs). Melting point: equal to or higher than 250° C.
7-(6-Amino-3-pyridyl)-1-cyclopropyl-8-methyl-4-oxo-1,4-dihydro-3-quinolinecarboxylic acid IR (KBr) cm$^{-1}$: 3448, 3342, 1706, 1627, 1610; NMR (CDCl$_3$) δ: 1.2–2.0 (4H, m), 3.12 (3H, s), 4.7–5.1 (1H, m), 7.42 (1H, d, J=9.5 Hz), 7.96 (1H, d, J=8.5 Hz), 8.0–8.4 (2H, m), 8.79 (1H, d, J=8.5 Hz), 9.76 (1H, s). Melting point: equal to or higher than 250° C.
7-(6-Amino-5-methyl-3-pyridyl)-1-cyclopropyl-8-methyl-4-oxo-1,4-dihydro-3-quinolinecarboxylic acid IR (KBr) cm$^{-1}$: 3379, 1730; NMR (CDCl$_3$) δ: 0.9–1.4 (4H, m), 2.14 (3H, s), 2.71 (3H, s), 4.2–4.6 (1H, m), 5.9–6.1 (2H, brs), 7.4–7.6 (2H, m), 7.9–8.0 (1H, brs), 8.18 (1H, d, J=8.3 Hz), 8.87 (1H, s), 15.00(1H, brs). Melting point: equal to or higher than 250° C.
1-Cyclopropyl-7-(2,6-dimethyl-4-pyridyl)-8-methyl-4-oxo-1,4-dihydro-3-quinolinecarboxylic acid N(Py)-oxide IR (KBr) cm$^{-1}$: 1724; NMR (CDCl$_3$) δ: 1.0–1.7 (4H, m), 2.63 (6H, s), 2.74 (3H, s), 4.0–4.4 (1H, m), 7.0–7.6 (3H, m), 8.34 (1H, d, J=8.1 Hz), 9.00 (1H, s), 14.4–14.6 (1H, brs). Melting point: equal to or higher than 250° C.
7-[6-({[(Benzyloxy)carbonyl](methyl)amino}methyl)-5-methyl-3-pyridyl]-1-cyclopropyl-8-methyl-4-oxo-1,4-dihydro-3-quinolinecarboxylic acid IR (KBr) cm$^{-1}$: 1708; NMR (CDCl$_3$) δ: 0.9–1.5 (4H, m), 2.41 (3H, s), 2.70 (3H, s), 3.06 (3H, s), 4.0–4.3 (1H, m), 4.71 (2 H, s), 5.20 (2H, s), 7.2–7.6 (7H, m), 8.3–8.6 (2H, m), 9.01 (1H, s), 14.5–14.8 (1H, brs).
1-Cyclopropyl-7-(4,6-dimethyl-3-pyridyl)-8-methyl-4-oxo-1,4-dihydro-3-quinolinecarboxylic acid IR (KBr) cm$^{-1}$: 1726; NMR (CDCl$_3$) δ: 0.9–1.6 (4H, m), 2.19 (3H, s), 2.57 (3H, s), 2.74 (3H, s), 4.0–4.6 (1H, m), 7.2–7.5 (2H, m), 8.3–8.6 (2H, m), 9.01 (1H, s), 14.5–14.6 (1H, brs). Melting point: 217° C.

1-Cyclopropyl-8-methyl-4-oxo-7-(3-pyridyl)-1,4-dihydro-3-quinolinecarboxylic acid IR (KBr) cm$^{-1}$: 1718; NMR (CDCl$_3$) δ: 1.0–1.6 (4H, m), 2.71 (3H, s), 4.0–4.4 (1H, m), 7.2–7.9 (3H, m), 8.42 (1H, d, J=7.8 Hz), 8.6–9.0 (2H, m), 9.02 (1H, s), 14.5–14.7 (1H, brs). Melting point: 247° C.

1-Cyclopropyl-7-(6-methyl-3-pyridyl)-8-methyl-4-oxo-1,4-dihydro-3-quinolinecarboxylic acid IR (KBr) cm$^{-1}$: 1726, 1613; NMR (CDCl$_3$) δ: 1.0–1.5 (4H, m), 2.67 (3H, s), 2.72 (3H, s), 4.1–4.3 (1H, m), 7.3–7.5 (2H, m), 7.66 (1H, dd, J=8.2 Hz), 8.37 (1H, d, J=8 Hz), 8.55 (1H, d, J=2 Hz), 8.99 (1H, s), 14.65 (1H, brs). Melting point: equal to or higher than 250° C.

1-Cyclopropyl-7-(5-methyl-3-pyridyl)-8-methyl-4-oxo-1,4-dihydro-3-quinolinecarboxylic acid IR (KBr) cm$^{-1}$: 1725, 1612; NMR (CDCl$_3$) δ: 1.0–1.5 (4H, m), 2.47 (3H, s), 2.65 (3H, s), 4.1–4.3 (1H, m), 7.4–7.6 (2H, m), 8.3–8.6 (3H, m), 9.01 (1H, s), 14.65 (1H, brs). Melting point: 231.5–232.5° C.

1-Cyclopropyl-7-[5-(hydroxymethyl)-3-pyridyl]-8-methyl-4-oxo-1,4-dihydro-3-quinolinecarboxylic acid IR (KBr) cm$^{-1}$: 1718, 1610; NMR (DMSO-d$_6$) δ: 0.6–1.5 (4H, m), 2.69 (3H, s), 4.3–4.6 (1H, m), 4.66 (2H, d, J=6 Hz), 5.46 (1H, t, J=6 Hz), 7.54 (1H, d, J=8.1 Hz), 7.85 (1H, s), 8.28 (1H, d, J=8.1 Hz), 8.5–8.7 (2H, m), 8.93 (1H, s). Melting point: 221–223° C.

1-Cyclopropyl-7-(5,6-diamino-3-pyridyl)-8-methyl-4-oxo-1,4-dihydro-3-quinolinecarboxylic acid NMR(DMSO-d$_6$) δ: 0.7–1.5 (4H, m), 2.72 (3H, s), 4.3–4.5 (1H, m), 4.8–5.0 (2H, brs), 5.6–5.8 (2H, brs), 6.86 (1H, s), 7.4–7.6 (2H, m), 8.1–8.3 (1H, m), 8.90 (1H, s).

1-Cyclopropyl-7-[6-(2-methylhydrazino)-3-pyridyl]-8-methyl-4-oxo-1,4-dihydro-3-quinolinecarboxylic acid IR (KBr) cm$^{-1}$: 1718; NMR (CDCl$_3$) δ: 0.8–1.8 (4H, m), 2.73 (3H, s), 3.38 (3H, s), 3.9–4.3 (3H, m), 7.0–7.7 (3H, m), 8.21 (1H, d, J=2.2 Hz), 8.37 (1H, d, J=8.8 Hz), 9.00 (1H, s). Melting point: 246° C.

1-Cyclopropyl-7-(2,6-dimethyl-4-pyridyl)-8-(difluoromethoxy)-4-oxo-1,4-dihydro-3-quinolinecarboxylic acid IR (KBr) cm$^{-1}$: 1724, 1610; NMR (CDCl$_3$) δ: 1.0–1.5 (4H, m), 2.65 (6H, s), 4.1–4.3 (1H, m), 5.98 (1H, t, J=74 Hz), 7.19 (2H, s), 7.58 (1H, d, J=8.6 Hz), 8.50 (1H, d, J=8.6 Hz), 8.98 (1H, s), 14.30 (1H, brs). Melting point: equal to or higher than 250° C.

7-(6-Amino-5-methyl-3-pyridyl)-1-cyclopropyl-8-methoxy-4-oxo-1,4-dihydro-3-quinolinecarboxylic acid IR (KBr) cm$^{-1}$: 3380, 1736, 1609; NMR (DMSO-d$_6$) δ: 1.0–1.3 (4H, m), 2.14 (3H, s), 3.42 (3H, s), 4.1–4.3 (1H, m), 6.08 (2H, s), 7.5–7.7 (2H, m), 8.1–8.3 (2H, m), 8.79 (1H, s). Melting point: equal to or higher than 250° C.

7-[6-Amino-5-methyl-3-pyridyl]-1-cyclopropyl-8-(difluoro-methoxy)-4-oxo-1,4-dihydro-3-quinolinecarboxylic acid IR (KBr) cm$^{-1}$: 3328, 1718; NMR (CDCl$_3$) δ: 1.0–1.6 (4H, m), 2.13 (3H, s), 4.0–4.4 (1Hr m), 6.16 (2H, s), 6.70 (1H, t, J=74.0 Hz), 7.55 (1H, m), 7.71 (1H, d, J=8.3 Hz), 8.12 (1H, m), 8.28 (1H, d, J=8.3 Hz), 8.86 (1H, s), 14.70 (1H, brs). Melting point: equal to or higher than 250° C.

EXAMPLE 4

A suspension of 1.80g of 7-{6-[acetyl(methyl)amino]-5-methyl-3-pyridyl}-1-cyclopropyl-8-methyl-4-oxo-1,4-dihydro-3-quinolinecarboxylic acid in 9 ml of concentrated hydrochloric acid and 36 ml of water was refluxed for 2hours and the precipitated crystals were filtered. The obtained crystals were dissolved in a mixed solvent consisting of 18 ml of water, 18 ml of an aqueous 1 mol/l sodium hydroxide solution and 18 ml of ethanol. Addition of 18 ml of 1 mol/l hydrochloric acid and filtration of precipitated crystals afforded 1.38 g of pale yellow crystals of 1-cyclopropyl-8-methyl-7-[5-methyl-6-(methylamino)-3-pyridyl]-4-oxo-1,4-dihydro-3-quinolinecarboxylic acid.

IR (KBr) cm$^{-1}$: 3410, 1713; NMR (DMSO-d$_6$) δ: 0.9–1.5 (4H, m), 2.17 (3H, s), 2.75 (3H, s), 2.97 (3H, d, J=4.6 Hz), 4.2–4.6 (1H, m), 5.9–6.2 (1H, m), 7.3–7.4 (1H, brs), 7.45 (1H, d, J=8.4 Hz), 7.9–8.1 (1H, brs), 8.23 (1H, d, J=8.4 Hz), 8.94 (1H, s), 15.00 (1H, brs). Melting point: equal to or higher than 250° C.

Similarly, the following compound was obtained.
1-Cyclopropyl-8-methyl-7-[6-(methylamino)-3-pyridyl]-4-oxo-1,4-dihydro-3-quinolinecarboxylic acid IR (KBr) cm$^{-1}$: 3237, 1727; NMR (DMSO-d$_6$) δ: 0.9–1.4 (4H, m), 2.72 (3H, s), 2.85 (3H, d, J=4.6 Hz), 4.2–4.6 (1H, m), 6.59 (1H, d, J=8.6 Hz), 6.7–6.8 (1H, m), 7.4–7.6 (2H, m), 8.1–8.3 (2H, m), 8.89 (1H, s), 15.00 (1H, brs). Melting point: equal to or higher than 250° C.

EXAMPLE 5

To a solution of 0.80 g of 7-[6-({[(benzyloxy)-carbonyl](methyl)amino}methyl)-5-methyl-3-pyrdyl]-1-cyclopropyl-8-methyl-4-oxo-1,4-dihydro-3-quinoline-carboxylic acid in 16 ml of acetic acid was added 0.20 g of 5% (w/w) palladium-carbon and the mixture was stirred at ambient temperature and atmospheric pressure for 2 hours under a hydrogen atmosphere. The reaction mixture was filtered and the solvent was evaporated under reduced pressure. The obtained residue was dissolved in a mixed solvent consisting of 3.8 ml of ethanol and 3.8 ml of water. After adding 3.8 ml of an aqueous 1 mol/l sodium hydroxide solution thereto and adjusting the solution to pH 5.5with 1 mol/l hydrochloric acid, 10 ml of chloroform was added thereto. An organic layer was separated and dried over anhydrous magnesium sulfate and the solvent was evaporated under reduced pressure. Addition of diethyl ether to the obtained residue and filtration of crystals afforded 0.25 g of colorless crystals of 1-cyclopropyl-8-methyl-7-{5-methyl-6-[(methylamino)methyl]-3-pyridyl}-4-oxo-1,4-dihydro-3-quinolinecarboxylic acid.

IR (KBr) cm$^{-1}$: 3322, 1721; NMR(d$_1$-TFA) δ: 1.2–1.9 (4H, m), 2.94 (3H, s), 3.05 (3H, s), 3.29 (3H, s), 4.6–5.0 (1H, m), 5.12 (2H, s), 7.91 (1H, d, J=8.5 Hz), 8.6–9.0 (2H, m), 9.0–9.3 (1H, brs), 9.75 (1H, s). Melting point: 199° C.

EXAMPLE 6

To a suspension of 0.37 g of 5-{[(benzyloxy)-carbonyl]amino}-1-cyclopropyl-7-(2,6-dimethyl-4-pyridyl)-8-methyl-4-oxo-1,4-dihydro-3-quinolinecarboxylic acid ethyl ester in 3.7 ml of ethanol was added 3.7 ml of an aqueous 1 mol/l sodium hydroxide solution and the mixture was stirred at 40° C. for 1 hour. After adding 3.7 ml of 1 mol/l hydrochloric acid to the reaction mixture, it was extracted with methylene chloride. The extract was dried over anhydrous magnesium sulfate and the solvent was evaporated under reduced pressure to obtain 0.34 g of yellow solids, which were suspended in 6.8 ml of 30% (W/V) hydrogen bromide acetic acid solution and the suspension was stirred at room temperature for 4 hours. The precipitated crystals were filtered and dissolved in a saturated sodium bicarbonate solution and the solution was extracted with chloro form. The obtained extract was dried over anhydrous magnesium sulfate and the solvent was evaporated under reduced pressure. The obtained residue was dissolved in a mixed solvent consisting of 1 ml of ethanol, 1 ml of water and 1 ml of an aqueous 1 mol/l sodium hydroxide solution, into which carbon dioxide gas was blown. Filtration of the precipitated crystals afforded 0.14 g of yellow solids of 5-amino-1-cyclopropyl-7-(2,6-dimethyl-4-pyridyl)-8-methyl-4-oxo-1,4-dihydro-3-quinolinecarboxylic acid.

IR (KBr) cm$^{-1}$: 3434, 1702; NMR (CDCl$_3$) δ: 0.9–1.4 (4H, m), 2.37 (3H, s), 2.61 (6H, s), 3.9–4.1 (1H, m), 6.44 (1H, s), 6.6–6.8 (2H, brs), 6.93 (2H, s), 8.85 (1H, s). Melting point: equal to or higher than 250° C.

Similarly, the following compound was obtained.
5-Amino-1-cyclopropyl-7-(5,6-dimethyl-3-pyridyl)-8-methyl-4-oxo-1,4-dihydro-3-quinolinecarboxylic acid IR (KBr) cm$^{-1}$: 3434, 1706; NMR (CDCl$_3$) δ: 0.9–1.4 (4H, m), 2.40 (6H, s), 2.59 (3H, s), 3.9–4.1 (1H, m), 6.49 (1H, s), 6.6–6.9 (2H, brs), 7.4–7.5 (1H, brs), 8.3–8.4 (1H, brs), 8.84 (1H, s). Melting point: equal to or higher than 250° C.

EXAMPLE 7

To a suspension of 0.36 g of 7-5{-[(benzyloxy)-carbonyl]amino}-3-pyridyl)-1-cyclopropyl-8-methyl-4-oxo-1,4-dihydro-3-quinolinecarboxylic ethyl ester in 3.6 ml of ethanol was added 3.6 ml of an aqueous 1 mol/l sodium hydroxide solution. The mixture was stirred at room temperature for 2 hours. To the reaction mixture was added 3.6 ml of 1 mol/l hydrochloric acid and precipitated crystals were filtered to obtain 0.28 g of pale yellow solids. The solids were suspended in 5.6 ml of 30% (W/V) hydrogen bromide acetic acid solution and the mixture was stirred at room temperature for 3 hours. The reaction mixture was concentrated under reduced pressure, ethanol and diethyl ether were added to the obtained residue, and crystals formed were filtered. The crystals were dissolved in 2 ml of a mixed solvent consisting of 2 ml of ethanol, 2 ml of water and 2 ml of an aqueous 1 mol/l sodium hydroxide solution and carbon dioxide gas was blown into the solution. Filtration of the precipitated crystals afforded 83 mg of colorless solids of 7-(5-amino-3-pyridyl)-1-cyclopropyl-8-methyl-4-oxo-1,4-dihydro-3-quinolinecarboxylic acid.

IR (KBr) cm$^{-1}$: 3427, 1716; NMR (d$_1$-TFA) δ: 1.2–1.8 (4H, m), 3.00 (3H, s), 4.7–4.9 (1H, m), 7.8–8.0 (2h, m), 8.1–8.3 (1H, brs), 8.3–8.4 (1H, brs), 8.73 (1H, d, J=8.5 Hz), 9.68 (1H, s). Melting point: equal to or higher than 250° C.

EXAMPLE 8

To a solution of 2.47 g of 1-cyclopropyl-7-(2,6-dimethyl-4-pyridyl)-8-methyl-4-oxo-1,4-dihydro-3-quinolinecarboxylic acid ethyl ester in 25 ml of methylene chloride was added m-chloroperbenzoic acid (70to 75%, 2.10 g) and the mixture was stirred at room temperature for 2 hours. The reaction mixture was washed with a saturated sodium bicarbonate solution and with a saturated saline solution in order and dried over anhydrous magnesium sulfate and the solvent was evaporated under reduced pressure. Purification of the obtained residue by column chromatography [eluent; chloroform:ethanol=30:1], addition of diethyl ether and filtration of crystals afforded 1.65 g of pale yellow crystals of 4-[1-cyclopropyl-3-(ethoxy-carbonyl)-8-methyl-4-oxo-1,4-dihydro-7-quinolyl]-2,6-dimethyl-1-pyridiniumolate [1-cyclopropyl-7-(2,6-dimethyl-4-pyridyl)-8-methyl-4-oxo-1,4-dihydro-3-quinolinecarboxylic acid ethyl ester N(Py)-oxide].

IR (KBr) cm$^{-1}$: 1729; NMR (CDCl$_3$) δ: 0.8–1.5 (7H, m), 2.61 (6H, s), 2.64 (3H, s), 3.9–4.2 (1H, m), 4.41 (2H, q, J=6.8 Hz), 7.1–7.4 (3H, m), 8.36 (1H, d, J=8.5 Hz), 8.74 (1H, s).

Similarly, the following compound was obtained.
1-Cyclopropyl-7-(5,6-dimethyl-3-pyridyl)-8-methyl-4-oxo-1,4-dihydro-3-quinolinecarboxylic acid ethyl ester N(Py)-oxide IR (KBr) cm$^{-1}$: 1685, 1636, 1607; NMR (CDCl$_3$) δ: 0.8–1.6 (7H, m), 2.44 (3H, s), 2.59 (3H, s), 2.64 (3H, s), 3.9–4.1 (1H, m), 4.41 (2H, q, J=7.1 Hz), 7.0–7.2 (1H, brs), 7.25(1H, d, J=8.0 Hz), 8.2–8.3 (1H, brs), 8.37 (1H, d, J=8.0 Hz), 8.73 (1H, s).

EXAMPLE 9

A suspension of 2.20 g of 1-cyclopropyl-7-(2,6-dimethyl-4-pyridyl)-8-methyl-4-oxo-1,4-dihydro-3-quinolinecarboxylic acid ethyl ester N(Py)-oxide in 7 ml of acetic anhydride was stirred at 100° C. for 30 minutes. The reaction mixture was concentrated under reduced pressure and a mixed solvent consisting of 50 ml of water and 50 ml of ethyl acetate was added to the obtained residue. The mixture was adjusted to pH 7with a saturated sodium bicarbonate solution and dried over magnesium sulfate and an organic layer was separated. The separated organic layer was washed with saturated saline and dried over magnesium sulfate and the solvent was evaporated under reduced pressure. After purifying the obtained residue by column chromatography (eluent; chloroform:ethanol=50:1], diisopropyl ether was added thereto and crystals were filtered. The crystals were dissolved in 6 mol/l hydrochloric acid and the solution was refluxed for 3 hours. The reaction mixture was concentrated under reduced pressure and a mixed solvent consisting of 20 ml of water, 20 ml of chloroform was added to the obtained residue, and the mixture was adjusted to pH 6.5with a saturated sodium bicarbonate solution, followed by filtration of precipitated crystals. After drying the obtained crystals and then purifying them by column chromatography [eluent; chloroform:ethanol=20:1], diisopropyl ether was added thereto. Filtration of the crystals afforded 0.87 g of colorless crystals of 1-cyclopropyl-7-[2-(hydroxymethyl)-6-methyl-4-pyridyl]-8-methyl-4-oxo-1,4-dihydro-3-quinolinecarboxylic acid.

IR (KBr) cm$^{-1}$: 3406, 1720; NMR (d$_6$-TFA) δ: 1.2–1.9 (4H, m), 3.04 (6H, s), 4.6–5.0 (1H, m), 5.41 (2H, s), 7.7–8.1 (3H, m), 8.80 (1H, d, J=7.2 Hz), 9.73 (1H, s).

Similarly, the following compound was obtained.
1-cyclopropyl-7-[6-(hydroxymethyl)-5-methyl-3-pyridyl]-8-methyl-4-oxo-1,4-dihydro-3-quinolinecarboxylic acid IR (KBr) cm$^{-1}$: 3460, 1724; NMR (CDCl$_3$) δ: 1.0–1.5 (4H, m), 2.35 (3H, s), 2.72 (3H, s), 4.1–4.3 (1H, m), 4.6–5.0 (3H, m), 7.4–7.6 (2H, m), 8.3–8.5 (2H, m), 9.01 (1H, s), 14.60 (1H, brs). Melting point: 225–226° C.

EXAMPLE 10

To a suspension of 0.20 g of 1-cyclopropyl-7-[2-(hydroxymethyl)-6-methyl-4-pyridyl]-8-methyl-4-oxo-1,4-dihydro-3-quinolinecarboxylic acid in 4 ml of dimethylformamide were added 0.09 g of potassium carbonate and 0.04 ml of ethyl iodide and the mixture was stirred at room temperature for 24 hours. The reaction mixture was added to a mixed solvent consisting of 10 ml of water and 10 ml of ethyl acetate and an organic layer was separated. The separated organic layer was washed with water and with saturated saline in order and dried over anhydrous magnesium sulfate and the solvent was evaporated under reduced pressure. Addition of diethyl ether to the obtained residue and filtration of crystals afforded 0.15 g of colorless crystals of 1-cyclopropyl-7-[2-(hydroxymethyl)-6-methyl-4-pyridyl]-8-methyl-4-oxo-1,4-dihydro-3-quinolinecarboxylic acid ethyl ester.

IR (KBr) cm$^{-1}$: 3397, 1702; NMR (CDCl$_3$) δ: 0.8–1.6 (7H, m), 2.62 (3H, s), 2.73 (3H, s), 3.8–4.8 (4H, m), 4.89 (2H, s), 7.1–7.3 (3H, m), 8.36(1H, d, J=8.1 Hz), 8.74 (1H, s).

EXAMPLE 11

To a solution of 0.17 g of 1-cyclopropyl-7-[2-(hydroxymethyl)-6-methyl-4-pyridyl]-8-methyl-4-oxo-1,4-dihydro-3-quinolinecarboxylic acid ethyl ester in 2 ml of methylene chloride was added 0.062 ml of thionyl chloride under ice cooling and the mixture was stirred at the same temperature for 30 minutes. The reaction mixture was concentrated under reduced pressure and added to a mixed solvent consisting of 10 ml of water and 10 ml of methylene chloride. After adjusting the reaction mixture to pH 8 with a saturated sodium bicarbonate solution, an organic layer was separated. The separated organic layer was dried over anhydrous magnesium sulfate and the solvent was evaporated under reduced pressure. Addition of diisopropyl ether to the obtained residue and filtration of crystals afforded 0.17 g of colorless crystals of 7-[2-(chloromethyl)-6-methyl-4-pyridyl]-1-cyclopropyl-8-methyl-4-oxo-1,4-dihydro-3-quinolinecarboxylic acid ethyl ester.

IR (KBr) cm$^{-1}$: 1700; NMR (CDCl$_3$) δ: 0.8–1.6 (7H, m), 2.62 (3H, s), 2.69 (3H, s), 3.9–4.2 (1H, m), 4.41(2H, q, J=7.1 Hz), 4.77 (2H, s), 7.1–7.4 (3H, m), 8.38(1H, d, J=8.3 Hz), 8.75 (1H, s).

EXAMPLE 12

To a suspension of 0.30 g of 7-[2-(chloromethyl)-6-methyl-4-pyridyl]-1-cyclopropyl-8-methyl-4-oxo-1,4-dihydro-3-quinolinecarboxylic acid ethyl ester in 5 ml of dimethyl formamide was added 0.24 g of potassium phthalimide and the mixture was stirred at 50° C. for 4 hours. After cooling the reaction mixture to room temperature, it was added to a mixed solvent consisting of 20 ml of water and 20 ml of ethyl acetate and an organic layer was separated. The separated organic layer was washed with saturated saline and dried over anhydrous magnesium sulfate and the solvent was evaporated under reduced pressure. Purification of the obtained residue by column chromatography [eluent; chloroform:ethanol=50:1] afforded 0.24 g of colorless crystals of 1-cyclopropyl-7-{2-[(1,3-dioxo-2,3-dihydro-1H-2-isoindolyl)methyl]-6-methyl-4-pyridyl}-8-methyl-4-oxo-1,4-dihydro-3-quinolinecaroxylic acid ethyl ester.

IR (KBr) cm$^{-1}$: 1770, 1716; NMR (CDCl$_3$) δ: 0.8–1.6 (7H, m), 2.56(3H, s), 2.63 (3H, s), 3.8–4.1 (1H, m), 4.40 (2H, q, J=7.3 Hz), 5.14 (2H, s), 7.0–7.4 (3H, m), 7.7–8.2 (4H, m), 8.33 (1H, d, J=8.3 Hz), 8.71 (1H, s).

EXAMPLE 13

To a suspension of 0.31 g of 1-cyclopropyl-7-{2-[(1,3-dioxo-2,3-dihydro-1H-2-isoindolyl)methyl]-6-methyl-4-pyridyl}-8-methyl-4-oxo-1,4-dihydro-3-quinolinecarboxylic acid ethyl ester in 2 ml of methanol was added 1.78 ml of an aqueous 1 mol/l sodium hydroxide solution and the mixture was stirred at room temperature for 1 hour. The reaction mixture was adjusted to pH 5.3 with 1 mol/l hydrochloric acid and then precipitated crystals were filtered. The obtained crystals were dissolved in 6 mol/l hydrochloric acid and the solution was stirred with heating at 100° C. for 4 hours. After cooling the reaction mixture to room temperature, insoluble matter was filtered off. The filtrate was concentrated under reduced pressure. Ethanol was added to the obtained residue and precipitates were filtered to obtain 0.15 g of 7-[2-(aminomethyl)-6-methyl-4-pyridyl]-1-cyclopropyl-8-methyl-4-oxo-1,4-dihydro-3-quinolinecarboxylic acid hydrochloride. The obtained hydrochloride was dissolved in a mixed solvent consisting of 1.2 ml of ethanol and 1.2 ml of water. After adding 1.2 ml of an aqueous 1 mol/l sodium hydroxide solution to the resulting solution, carbon dioxide gas was blown therein. Filtration of the precipitates afforded 0.10 g of colorless crystals of 7-[2-(aminomethyl)-6-methyl-4-pyridyl]-1-cyclopropyl- 8-methyl-4-oxo-1,4-dihydro-3-quinolinecarboxylic acid.

IR (KBr) cm$^{-1}$: 3414, 1637; NMR (d$_6$-TFA) δ: 1.3–2.0 (4H, m), 3.07 (6H, s), 4.6–5.0 (1H, m), 5.12 (2H, s), 7.86 (1H, d, J=9.2 Hz), 8.0–8.3 (1H, brs), 8.3–8.5 (1H, brs), 8.81 (1H, d, J=9.2 Hz), 9.75 (1H, s). Melting point: 150° C.

EXAMPLE 14

A suspension of 1.90 g of N-{5-[3-(cyclopropylamino)-2-methylphenyl]-3-methyl-2-pyridyl}-N,2,2-trimethylpropanamide in 1.29 g of diethyl ethoxymethylenemalonate was stirred at 130° C. for 14 hours. After evaporating ethanol generated, 10.96 g of polyphosphoric acid was added and the resulting mixture was stirred at 80° C. for 30 minutes. After cooling the reaction mixture to room temperature, 30 ml of water and 30 ml of chloroform were added thereto. After adjusting the reaction mixture to pH 6 with an aqueous 1 mol/l sodium hydroxide solution, an organic layer was separated. The obtained organic layer was washed with saturated saline and dried over anhydrous magnesium sulfate and the solvent was evaporated under reduced pressure. Addition of ethyl acetate to the obtained residue and filtration of crystals afforded 1.03 g of pale yellow crystals of 1-cyclopropyl-8-methyl-7-[5-methyl-6-(methylamino)-3-pyridyl]-4-oxo-1,4-dihydro-3-quinolinecarboxylic acid ethyl ester.

IR (KBr) cm$^{-1}$: 3391, 1729, 1606; NMR (CDCl$_3$) δ: 0.8–1.6 (7H, m), 2.18 (3H, s), 2.66 (3H, s), 3.12 (3H, d, J=4.6 Hz), 3.8–4.6 (4H, m), 7.1–7.5 (2H, m), 8.10 (1H, d, J=2.2 Hz), 8.23 (1H, d, J=8.1 Hz), 8.72 (1H, s).

EXAMPLE 15

To a suspension of 1.00 g of 1-cyclopropyl-8-methyl-7-[5-methyl-6-(methylamino)-3-pyridyl]-4-oxo-1,4-dihydro-3-quinolinecarboxylic acid ethyl ester in 10 ml of ethanol was added 10 ml of an aqueous 1 mol/l sodium hydroxide solution and then the mixture was stirred at 40° C. for 1 hour. Addition of 10 ml of 1 mol/l hydrochloric acid and filtration of crystals afforded 0.82 g of pale yellow crystals of 1-cyclopropyl-8-methyl-7-[5-methyl-6-(methylamino)-3-pyridyl]-4-oxo-1,4-dihydro-3-quinolinecarboxylic acid. The physical data coincided with those of the compound obtained in Example 4.

EXAMPLE 16

To a suspension of 30 g of 7-chloro-1-cyclopropyl-8-methyl-4-oxo-1,4-dihydro-3-quinolinecaroxylic acid ethyl ester in a mixed solvent consisting of 60 ml of water and 300 ml of toluene were added 31.9 g of 6-[(2,2-dimethylpropanoyl)(methyl)amino]-5-methyl-3-pyridyl borate, 24.7 g of sodium hydrogen carbonate and 1.81 g of bis(tricyclohexylphosphine)palladium (II) chloride and then the mixture was refluxed under a nitrogen atmosphere for 14 hours. After cooling the reaction mixture to room temperature, 120 ml of water was added thereto and precipitated crystals were filtered. After drying the obtained crystals, purification thereof by silica gel column chromatography [eluent; chloroform:ethanol=60:1] afforded 38.2 g of colorless crystals of 1-cyclopropyl-7-{6-[(2,2-dimethylpropanoyl) (methyl)-amino]-5-methyl-3-pyridyl}-8-methyl-4-oxo-1,4-dihydro-3-quinolinecarboxylic acid ethyl ester.

IR (KBr) cm$^{-1}$: 2987, 2965, 1727, 1611; NMR (CDCl$_1$) δ: 0.8–1.6 (16H, m), 2.38(3H, s), 2.65 (3H, s), 3.27 (3H, s), 3.9–4.2 (1H, m), 4.41 (2H, q, J=7.1 Hz), 7.32(1H, d, J=5.1 Hz), 7.64 (1H, d, J=2.0 Hz), 8.3–8.5 (2H, m), 8.74 (1H, s).

EXAMPLE 17

To a suspension of 0.50 g of 7-chloro-1-cyclopropyl-8-methyl-4-oxo-1,4-dihydro-3-quinolinecarboxylic acid ethyl ester in 5ml of 1,2-dimethoxyethane were added 0.85 g of N-[5-(1,3,2-dioxaborinan-2-yl)-3-methyl-2-pyridyl]-N,2,2-trimethylpropanamide, 1.04 g of tripotassium phosphate and 0.11 g of bis(triphenylphosphine)nickel (II) chloride and then the mixture was refluxed under a nitrogen atmosphere for 16 hours. The reaction mixture was added to a mixed solvent consisting of 10 ml of water and 10 ml of methylene chloride and an organic layer was separated. The separated organic layer was dried over anhydrous magnesium sulfate and then the solvent was evaporated under reduced pressure. Purification of the obtained residue by silica gel column chromatography [ethyl acetate] afforded 0.14 g of colorless crystals of 1-cyclopropyl-7-{6-[(2,2-dimethylpropanoyl) (methyl)amino]-5-methyl-3-pyridyl}-8-methyl-4-oxo-1,4-dihydro-3-quinolinecarboxylic acid ethyl ester. The physical data coincided with those of the compound obtained in Example 16.

EXAMPLE 18

1-Cyclopropyl-7-{6-[(2,2-dimethylpropanoyl)(methyl)-amino]-5-methyl-3-pyridyl}-8-methyl-4-oxo-1,4-dihydro-3-quinolinecarboxylic acid ethyl ester was treated in the same manner as in Example 3to obtain 1-cyclopropyl-7-{6-[(2,2-dimethylpropanoyl)(methyl)amino]-5-methyl-3-pyridyl}-8-methyl-4-oxo-1,4-dihydro-3-quinolinecarboxylic acid.

IR (KBr) cm$^{-1}$: 3553, 1723, 1616; NMR (CDCl$_3$) δ: 1.0–1.6 (13H, m), 2.41 (3H, s), 2.75 (3H, s), 3.28 (3H, s), 4.0–4.4 (1H, m), 7.46 (1H, d, J=8.3 Hz), 7.68 (1H, d, J=2.4 Hz), 8.3–8.5 (2H, m), 9.01 (1H, s), 14.5–14.7 (1H, brs), 14.60(1H, brs).

EXAMPLE 19

1-Cyclopropyl-7-{6-[(2,2-dimethylpropanoyl)(methyl)-amino]-5-methyl-3-pyridyl}-8-methyl-4-oxo-1,4-dihydro-3-quinolinecarboxylic acid was treated in the same manner as in Example 4to obtain 1-cyclopropyl-8-methyl-7-[5-methyl-6-(methylamino)-3-pyridyl]-4-oxo-1,4-dihydro-3-quinolinecarboxylic acid. The physical data coincided with those of the compound obtained in Example 4.

INDUSTRIAL APPLICABILITY

The compounds of the present invention exhibit potent antibacterial activity against gram-positive bacteria such as staphylococci, in particular Propionibacterium acnes. Furthermore, the present invention provides quinolone antimicrobial agents having high safety, e.g., decreased phototoxicity, mutagenicity, etc. and are useful as therapeutic agents for skin infections.

What is claimed is:

1. Quinolonecarboxylic acid derivatives or salts thereof represented by general formula

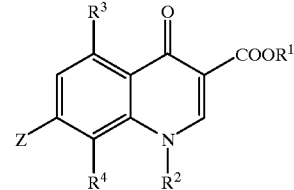

(wherein R$^1$ represents a hydrogen atom or a carboxyl-protective group; R$^2$ represents an optionally substituted cycloalkyl group; R$^3$ represents a hydrogen atom, a halogen atom, an optionally substituted alkyl, alkoxy or alkylthio group, an optionally protected hydroxyl or amino group, or a nitro group; R$^4$ represents an optionally substituted alkyl or alkoxy group; and Z represents a pyridin-4-yl or pyridin-3-yl group which is optionally substituted with at least one group selected from a halogen atom, an optionally substituted alkyl, alkenyl, cycloalkyl, alkoxy, alkylthio or amino group and an optionally protected hydroxyl or amino group).

2. The quinolonecarboxylic acid derivatives or salts thereof as claimed in claim 1, wherein R$^3$ represents a hydrogen atom, an optionally substituted alkyl group or an optionally protected amino group; and Z represents a pyridin-4-yl or pyridin-3-yl group substituted with an optionally substituted alkyl, alkoxy or amino group.

3. The quinolonecarboxylic acid derivatives or salts thereof as claimed in claim 1 or 2, wherein R$^2$ represents a cyclopropyl group; R$^3$ represents a hydrogen atom, an alkyl group or an amino group; and Z represents a pyridin-3-yl group substituted with an optionally substituted alkyl, alkoxy or amino group.

4. The quinolonecarboxylic acid derivatives or salts thereof as claimed in any one of claims 1 to 3, wherein R$^3$ represents a hydrogen atom; R$^4$ represents a methyl or methoxy group; and Z represents a pyridin-3-yl group substituted with at least one group selected from a methyl group, a hydroxymethyl group, an amino group, a methylamino group or a dimethylamino group.

5. 1-Cyclopropyl-7-(2,6-dimethyl-4-pyridyl)-8-methyl-4-oxo-1,4-dihydro-3-quinolinecarboxylic acid or salts thereof.

6. 1-Cyclopropyl-8-methyl-7-[5-methyl-6-(methylamino)-3-pyridyl]-4-oxo-1,4-dihydro-3-quinolinecarboxylic acid or salts thereof.

7. 7-(6-Amino-5-methyl-3-pyridyl)-1-cyclopropyl-8-methoxy-4-oxo-1,4-dihydro-3-quinolinecarboxylic acid or salts thereof.

* * * * *